United States Patent
Weeres

(10) Patent No.: US 11,802,756 B2
(45) Date of Patent: Oct. 31, 2023

(54) ICE THICKNESS TRANSDUCER

(71) Applicant: Steven R. Weeres, Richmond, MN (US)

(72) Inventor: Steven R. Weeres, Richmond, MN (US)

(*) Notice: Subject to any disclaimer, the term of this patent is extended or adjusted under 35 U.S.C. 154(b) by 215 days.

(21) Appl. No.: 17/402,537

(22) Filed: Aug. 14, 2021

(65) Prior Publication Data

US 2022/0406157 A1 Dec. 22, 2022

Related U.S. Application Data

(60) Provisional application No. 63/067,308, filed on Aug. 18, 2020.

(51) Int. Cl.
| | | |
|---|---|---|
| *G01R 33/00* | (2006.01) | |
| *G01B 7/06* | (2006.01) | |
| *G08B 5/38* | (2006.01) | |
| *G01N 33/18* | (2006.01) | |
| *G01B 7/26* | (2006.01) | |

(52) U.S. Cl.
CPC .............. *G01B 7/06* (2013.01); *G01B 7/26* (2013.01); *G01N 33/1886* (2013.01); *G08B 5/38* (2013.01); *G01N 2033/1873* (2013.01)

(58) Field of Classification Search
CPC .............. G01R 33/00; G01R 33/0035; G01R 33/0023; G01R 33/0017; G01R 31/3191; G01B 7/004; G01B 7/06; G01B 7/26; G01C 17/38; G06F 3/017; G06F 3/0346; G06F 3/012; G08B 5/38; G01N 2033/1873
See application file for complete search history.

(56) References Cited

U.S. PATENT DOCUMENTS

| | | | |
|---|---|---|---|
| 332,480 A | 12/1886 | Boyle | |
| 354,508 A | 12/1886 | Fraleigh | |
| 459,323 A | 9/1891 | Weuste | |
| 525,548 A | 9/1894 | Humberstone | |

(Continued)

OTHER PUBLICATIONS

Ashton, "Thin Ice Growth", Water Resources Research, vol. 25, No. 3, Mar. 1989, pp. 564-566, saved as "Ashton_Thin_Ice_Growth_Model_1989.pdf".

(Continued)

*Primary Examiner* — Jermele M Hollington
*Assistant Examiner* — Taqi R Nasir
(74) *Attorney, Agent, or Firm* — Albert W. Watkins

(57) ABSTRACT

A transducer for measuring the thickness of ice in a body of water includes a transducer body, at least one ice presence sensor for measuring the presence of ice at a point beyond a boundary layer between the transducer body and the body of water, a flotation element, a controller, and a display assembly. The transducer body includes waterproof membrane sealed orifices positioned on the transducer body for one or more ice presence sensors. A tether point attaches an anchor to keep the transducer at a fixed location in the water body. The ice presence sensor includes a sense probe passing through the waterproof membrane, a sense probe seal, a drive rod, a switch, and an actuator. The display includes one or more visible elements to indicate ice thickness at the transducer location. The ice thickness is inferred by the collective indications at the one or more ice presence sensors.

16 Claims, 8 Drawing Sheets

(56) References Cited

U.S. PATENT DOCUMENTS

| | | |
|---|---|---|
| 532,868 A | 1/1895 | Bull |
| 712,699 A | 11/1902 | May |
| 954,727 A | 4/1910 | Fryett et al. |
| 1,079,229 A | 11/1913 | Fitzgerald |
| 1,081,843 A | 12/1913 | Larson |
| 1,139,489 A | 5/1915 | Church |
| 1,154,162 A | 9/1915 | Baker |
| 1,162,699 A | 11/1915 | Kline, Jr. |
| 1,175,417 A | 3/1916 | Fehrenbach et al. |
| 1,179,486 A | 4/1916 | Wight |
| 1,224,741 A | 5/1917 | Hewis |
| 1,278,949 A | 9/1918 | Compte |
| 1,347,944 A | 7/1920 | Gervasoni et al. |
| 1,414,298 A | 4/1922 | Montero |
| 1,435,411 A | 11/1922 | Mitchell |
| 1,634,165 A | 6/1927 | Williams |
| 1,678,115 A | 7/1928 | Hanon |
| 1,979,546 A | 11/1934 | Heintz |
| 2,171,450 A | 8/1939 | Langley |
| 2,193,836 A | 3/1940 | Winther |
| 2,203,766 A | 6/1940 | Baer et al. |
| 2,210,775 A | 8/1940 | Perry |
| 2,216,069 A | 9/1940 | Doyle |
| 2,338,574 A | 1/1944 | Cunningham |
| 2,414,756 A | 1/1947 | May |
| 2,419,454 A | 4/1947 | Clair |
| 2,421,819 A | 6/1947 | Vandenberg |
| 2,427,778 A | 9/1947 | Gregg |
| 2,480,846 A | 9/1949 | Friedman et al. |
| 2,494,877 A | 1/1950 | Idrac |
| 2,541,512 A | 2/1951 | Hahn |
| 2,557,311 A | 6/1951 | Pond |
| 2,561,437 A | 7/1951 | Cobb |
| 2,577,779 A | 12/1951 | Lindberg |
| 2,622,923 A | 12/1952 | Cobb |
| 2,632,308 A | 3/1953 | Engelhardt |
| 2,775,678 A | 12/1956 | Flubacker |
| 2,775,679 A | 12/1956 | Flubacker |
| 2,775,680 A | 12/1956 | Flubacker |
| 2,786,927 A | 3/1957 | Veldhuis |
| 2,789,281 A | 4/1957 | Short et al. |
| 2,800,647 A | 7/1957 | Baerwald et al. |
| 2,803,813 A | 8/1957 | Bullen et al. |
| 2,820,958 A | 1/1958 | Fraser |
| 2,846,555 A | 8/1958 | Grieger |
| 2,874,259 A | 2/1959 | Morris |
| 2,901,741 A | 8/1959 | Moore et al. |
| 2,902,669 A | 9/1959 | Lucarelli |
| 2,961,842 A | 11/1960 | Wright |
| 3,002,186 A | 9/1961 | Schlangen |
| 3,091,680 A | 5/1963 | Adrig |
| 3,123,701 A | 3/1964 | Padgett, Jr. |
| 3,134,563 A | 5/1964 | Stuetzer |
| 3,233,078 A | 2/1966 | Siemianowski |
| 3,270,330 A | 8/1966 | Weinberg |
| 3,277,459 A | 10/1966 | Werner |
| 3,320,805 A | 5/1967 | Kahle |
| 3,341,835 A | 9/1967 | Werner et al. |
| 3,350,541 A | 10/1967 | Richardson |
| 3,484,774 A | 12/1969 | Borgnakke |
| 3,496,733 A | 2/1970 | Parker et al. |
| 3,502,899 A | 3/1970 | Jones |
| 3,523,456 A | 8/1970 | Matzen et al. |
| 3,541,540 A | 11/1970 | Hughes |
| 3,545,272 A | 12/1970 | McGill |
| 3,614,759 A | 10/1971 | Moore et al. |
| 3,621,714 A | 11/1971 | Puccinelli |
| 3,685,357 A | 8/1972 | Alexander |
| 3,706,981 A | 12/1972 | Hart |
| 3,781,566 A | 12/1973 | Meuller |
| 3,836,846 A | 9/1974 | Overall et al. |
| 3,882,381 A | 5/1975 | Gregory |
| 3,935,834 A | 2/1976 | Buhrmann, Jr. |
| 3,992,941 A | 11/1976 | McGoldrick |
| 4,054,255 A | 10/1977 | Magenheim |
| 4,086,812 A | 5/1978 | Luthe et al. |
| 4,125,022 A | 11/1978 | Sumida |
| 4,175,435 A | 11/1979 | Hara |
| 4,175,445 A | 11/1979 | Templeton, III |
| 4,175,512 A | 11/1979 | Iwanicki |
| 4,250,750 A | 2/1981 | Martinec et al. |
| 4,287,472 A | 9/1981 | Pan et al. |
| 4,303,984 A | 12/1981 | Houvig |
| 4,361,039 A | 11/1982 | van der Lely |
| 4,375,721 A | 3/1983 | Ueda |
| 4,384,282 A | 5/1983 | Dennison, Jr. |
| 4,418,570 A | 12/1983 | Warren, Jr. et al. |
| 4,426,885 A | 1/1984 | Visco |
| 4,459,584 A | 7/1984 | Clarkson |
| 4,461,178 A | 7/1984 | Chamuel |
| 4,470,123 A | 9/1984 | Magenheim et al. |
| 4,497,179 A | 2/1985 | Iwans |
| 4,532,806 A | 8/1985 | Bruchmueller |
| 4,551,982 A | 11/1985 | Kocher et al. |
| 4,553,137 A | 11/1985 | Marxer et al. |
| 4,568,922 A | 2/1986 | Schwippert et al. |
| 4,571,998 A | 2/1986 | Stegner |
| 4,611,492 A | 9/1986 | Koosmann |
| 4,628,736 A | 12/1986 | Kirby et al. |
| 4,638,640 A | 1/1987 | Whetstone et al. |
| 4,646,068 A | 2/1987 | Skala |
| 4,721,949 A | 1/1988 | Provencal et al. |
| 4,730,491 A | 3/1988 | Lew |
| 4,765,187 A * | 8/1988 | Weinstein ............ G01R 27/22 73/304 R |
| 4,775,118 A | 10/1988 | Daniels |
| 4,782,331 A | 11/1988 | Martens |
| 4,873,510 A | 10/1989 | Khurgin |
| 4,939,908 A | 7/1990 | Ewing et al. |
| 4,996,493 A | 2/1991 | Monat et al. |
| 5,021,769 A | 6/1991 | Schuellein |
| 5,022,233 A | 6/1991 | Kirschner et al. |
| 5,079,950 A | 1/1992 | McKiernan et al. |
| 5,103,673 A | 4/1992 | Sawada et al. |
| 5,134,380 A | 7/1992 | Jonas |
| 5,187,980 A | 2/1993 | Blair et al. |
| 5,446,448 A | 8/1995 | Zufelt et al. |
| 5,483,831 A | 1/1996 | Steiner |
| 5,507,183 A | 4/1996 | Larue et al. |
| 5,551,288 A | 9/1996 | Geraldi et al. |
| 5,606,864 A | 3/1997 | Jones |
| 5,710,554 A | 1/1998 | Pettler et al. |
| 5,955,887 A | 9/1999 | Codner et al. |
| 6,049,282 A | 4/2000 | Mackenzie |
| 6,253,557 B1 | 7/2001 | Credle, Jr. |
| 6,370,952 B1 | 4/2002 | Little et al. |
| 6,384,611 B1 * | 5/2002 | Wallace ............... B64D 15/20 324/699 |
| 6,425,286 B1 | 7/2002 | Anderson et al. |
| 6,456,197 B1 | 9/2002 | Lauritsen et al. |
| 6,532,814 B2 | 3/2003 | Bromley |
| 6,758,091 B1 | 7/2004 | Nielsen |
| 7,423,541 B2 | 9/2008 | Miller |
| 7,617,725 B2 | 11/2009 | Howayshell |
| 8,049,522 B2 | 11/2011 | Vadder et al. |
| 8,132,461 B2 | 3/2012 | Clasen et al. |
| 8,171,786 B2 | 5/2012 | Burris |
| 8,299,931 B2 | 10/2012 | Eggleston |
| 9,625,248 B2 | 4/2017 | Figueroa-Karlstrom |
| 10,066,923 B2 | 9/2018 | Go et al. |
| 2010/0052703 A1 | 3/2010 | Vadder et al. |
| 2011/0050429 A1 | 3/2011 | Eggleston |
| 2013/0238282 A1 * | 9/2013 | Figueroa-Karlstrom ............... B64D 15/20 702/170 |
| 2015/0260501 A1 | 9/2015 | Go et al. |

OTHER PUBLICATIONS

Brown, "A comparison of simulated and measured lake ice thickness using a Shallow Water Ice Profiler", Hydrol. Process. (2011), 10 Pgs, Wiley Online Library, saved as "BrownDuguay_Shallow_Water_Ice_Profile_2011.pdf".

(56) References Cited

OTHER PUBLICATIONS

"CS616 30 cm Water Content Reflectometer", Product, Jul. 8, 2020, 2 pgs, Campbell Scientific, Inc., saved as "b_cs616.pdf".

"CS616 and CS625 Water Content Reflectometers", Product Manual, May 2020, 41 pgs, Campbell Scientific, Inc., saved as "cs616.pdf".

Dibiasia et al; Design and Prototype of a Freshwater Ice Thickness Measuring Device, Apr. 25, 2017, 67 pages, Worcester Polytechnic Institute, saved as "Eggleston_Ice_Measuring_Device.pdf".

Lepparanta, "Modelling the Formation and Decay of Lake Ice", The Impact of Climate Change on European Lakes, 2010, pp. 63-83, Springer Science+Business Media B.V., saved as "Lepparanta_CLIME_Book_2010_CH5_Mod_ice_p63-83-1.pdf".

Reed et al, "Evaluation of Low-Cost, Automated Lake Ice Thickness Measurements", Journal of Atmospheric and Oceanic Technology, Apr. 2019, pp. 527-534, saved as "Reed Eval of Automated Methods 2019.pdf".

Polashenski et al, "Seasonal ice mass-balance buoys: adapting tools to the changing Arctic", Annals of Glaciology 52(57) 2011, pp. 18-26, saved as "SIMB_IGS_Final_remote_bouy.pdf".

"Quantifying Ice and Frost Buildup Using Capacitive Sensors", TI TechNotes, SNOA973, Dec. 2017, 3 pages, Texas Instruments Incorporated, saved as "Texas Instruments_Ice_Sensors.pdf".

Whitaker et al, "Lake ice measurements from soil water content reflectometer sensors", Limnol. Oceanogr.: Methods 14, 2016, pp. 224-230, saved as "Whitaker_Ice_Thickness_sensor.pdf".

Yoshikawa et al, "A simple equation for ice sheet thickness and ice formation/breakup prediction", Journal of JSCE, vol. 2, 2014, pp. 203-213, saved as "Yoshikawa_Ice_sheet_formation_2014.pdf".

\* cited by examiner

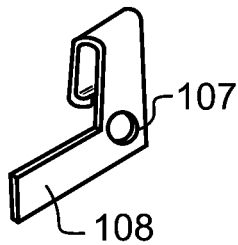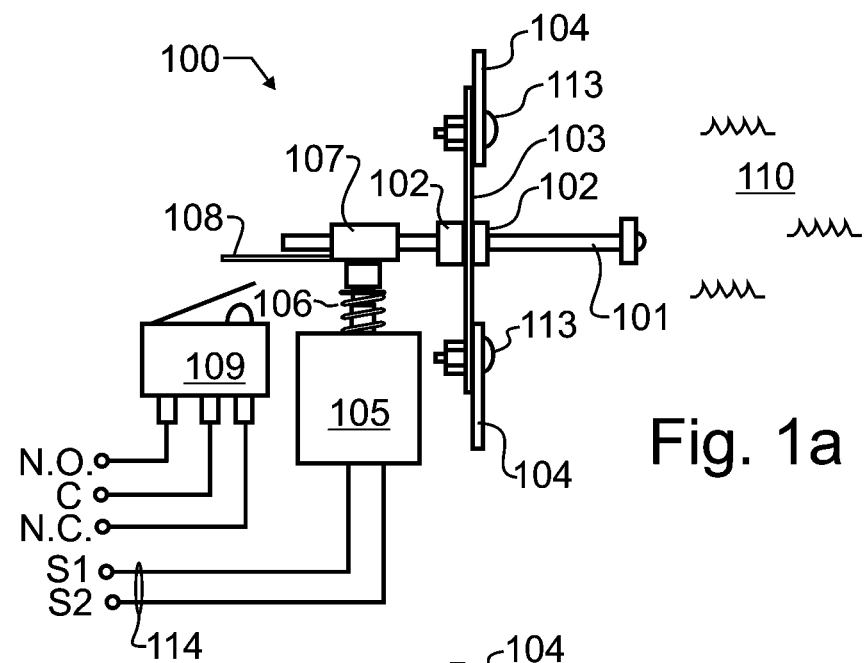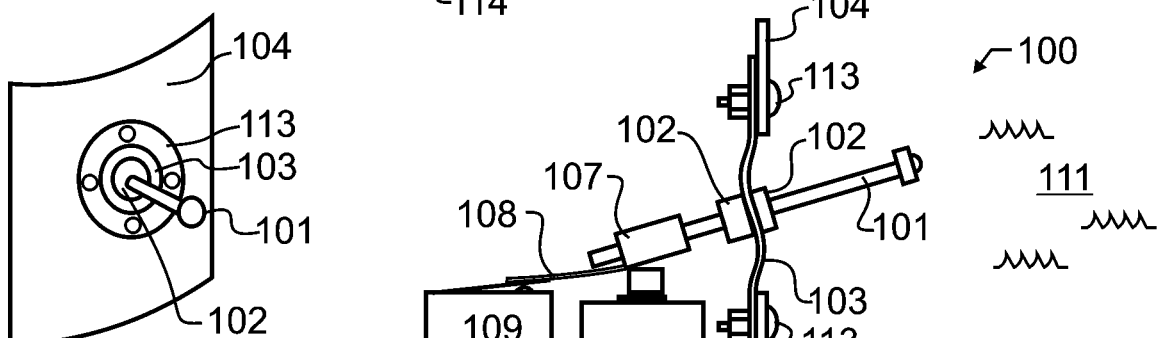

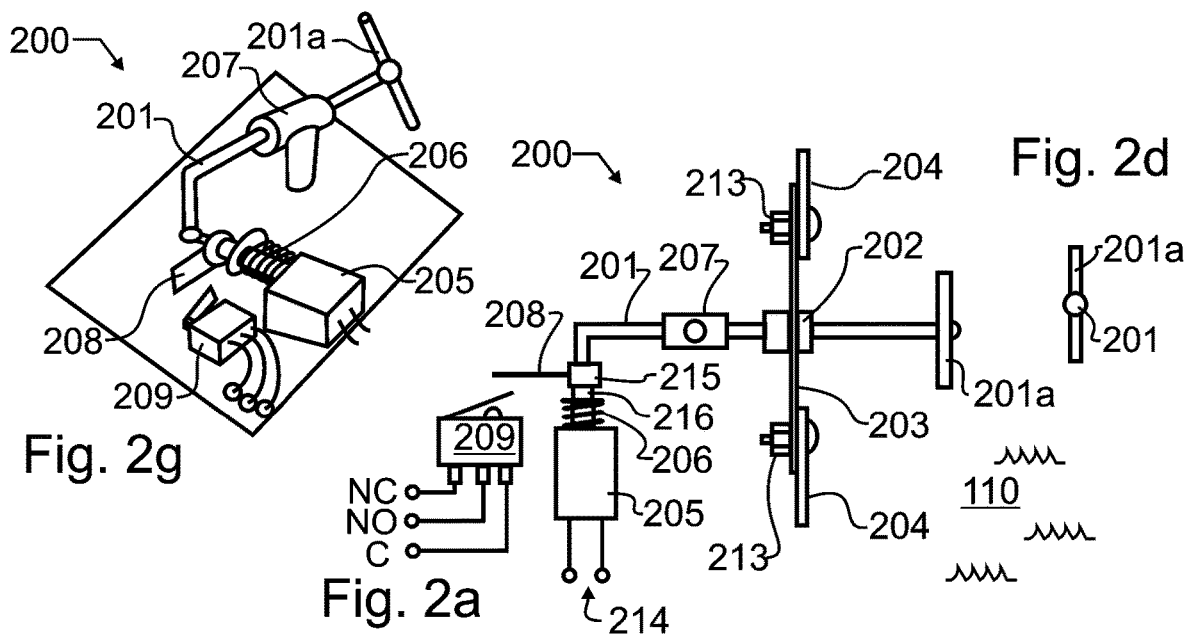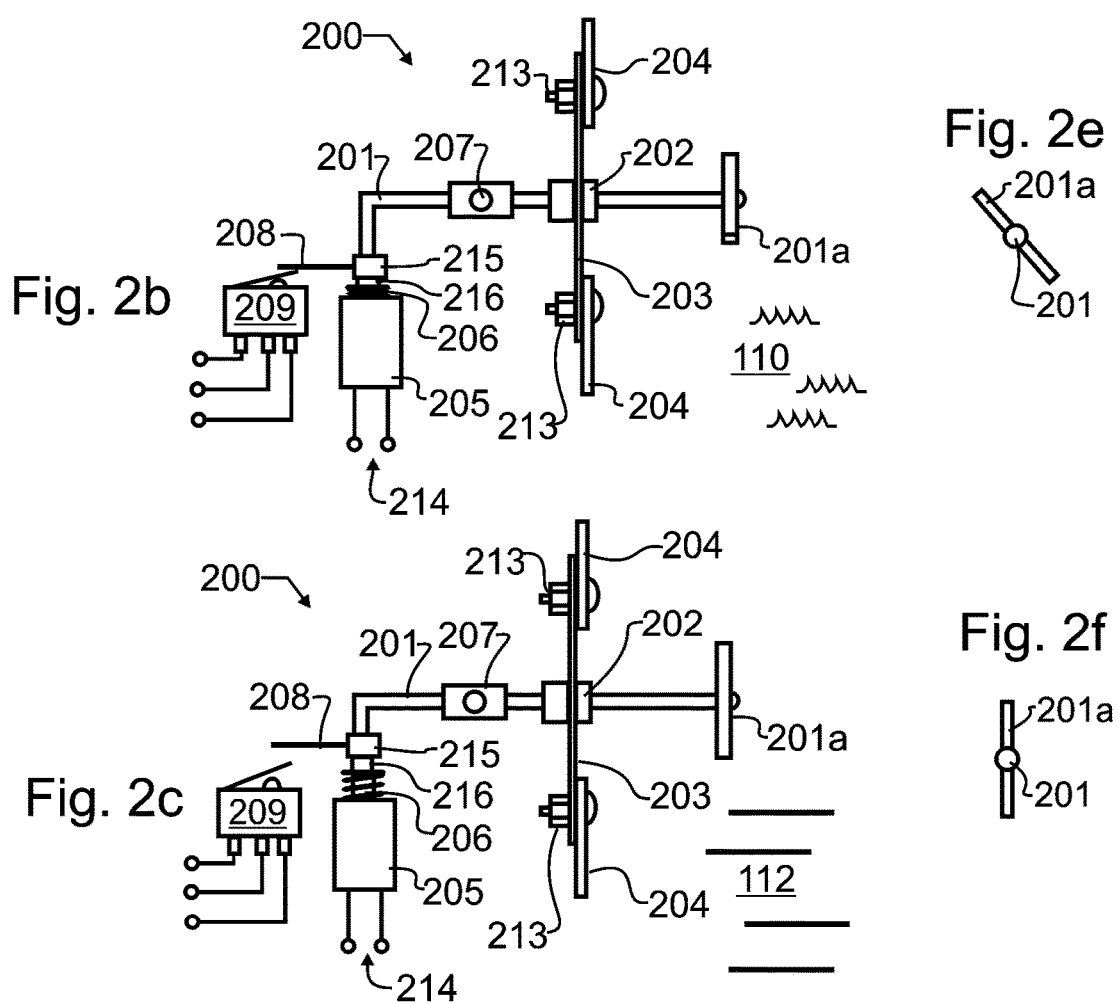

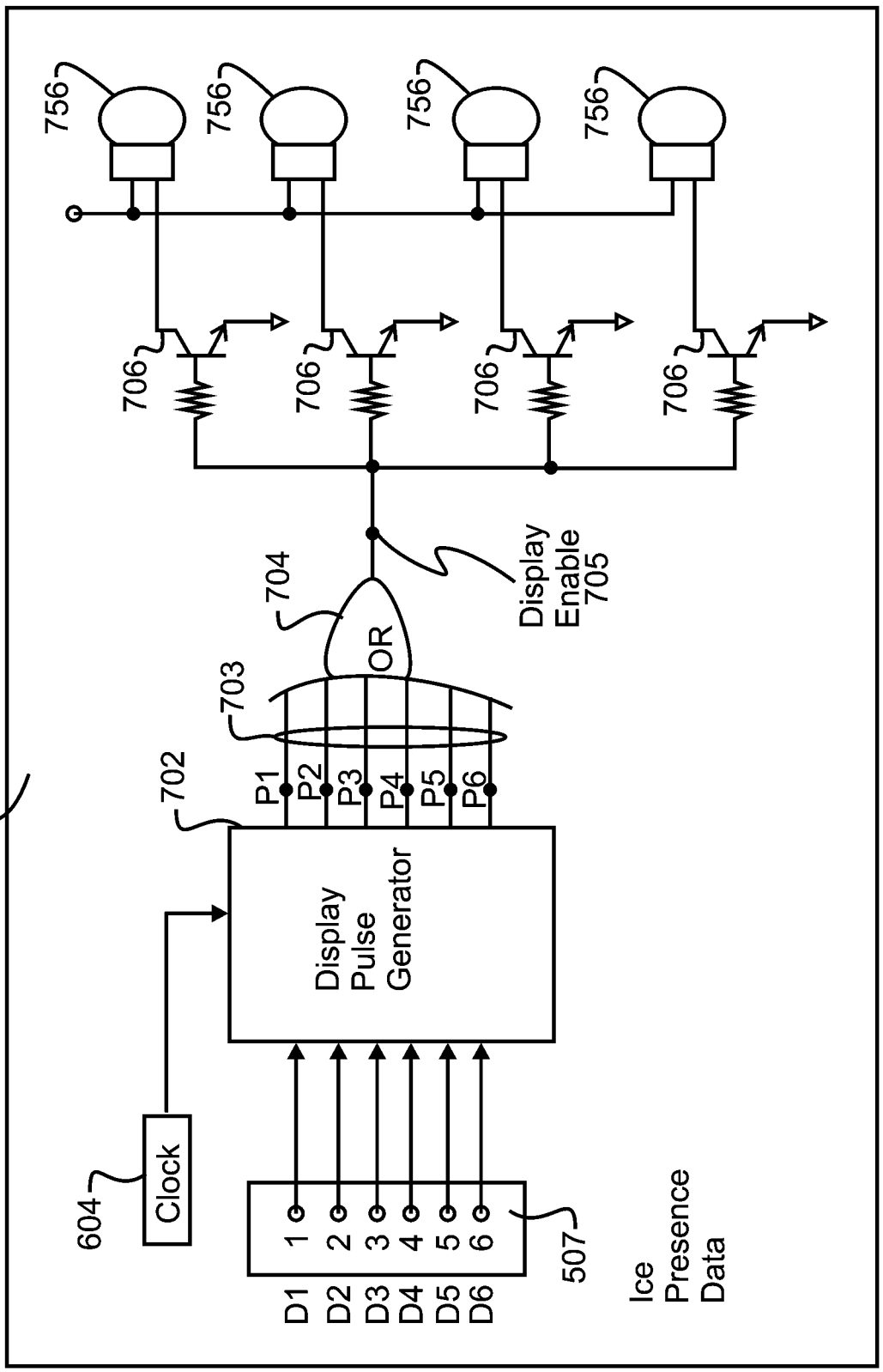

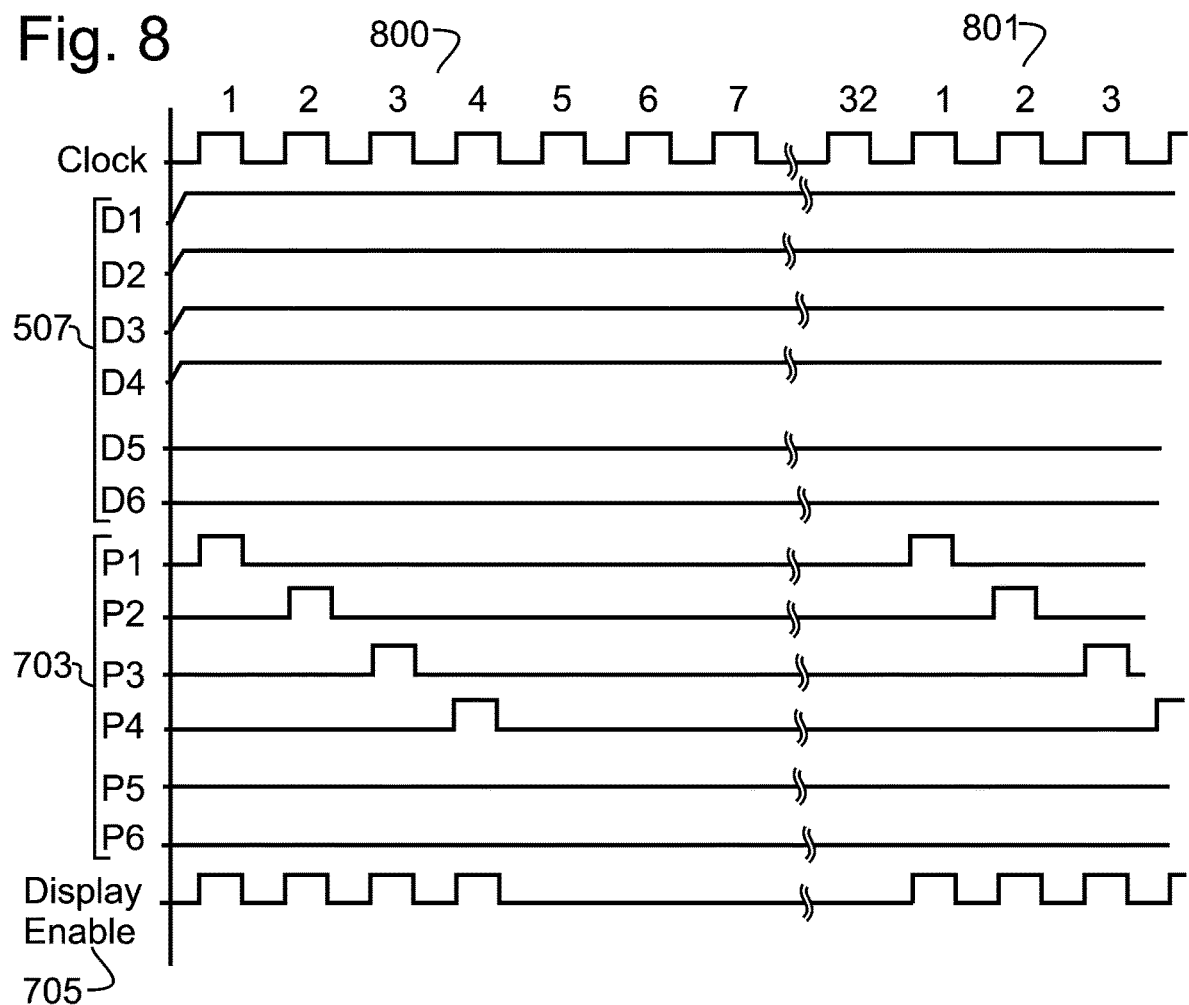
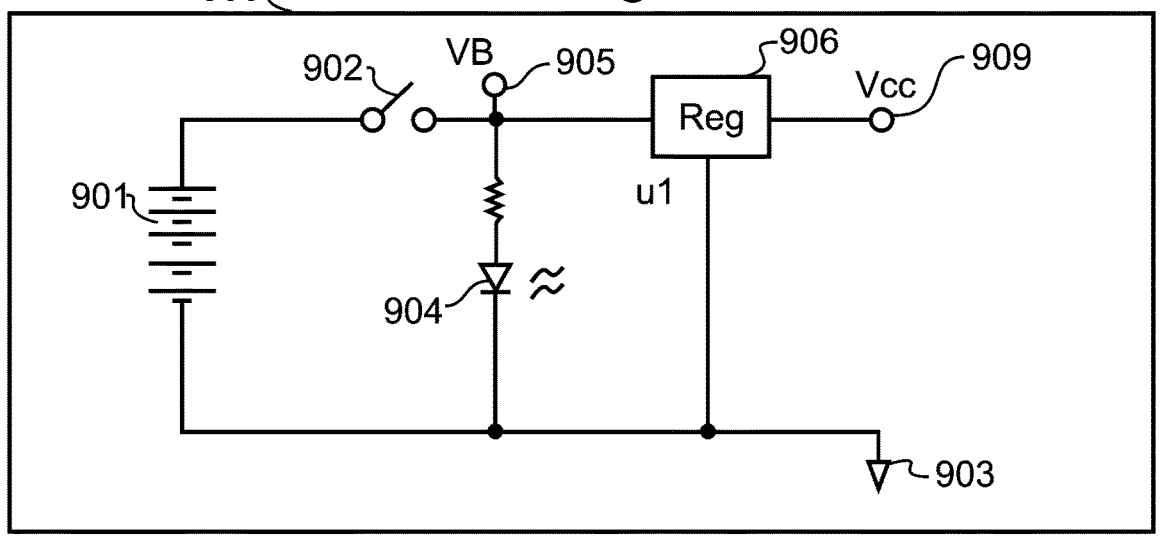

ICE THICKNESS TRANSDUCER

CROSS REFERENCE TO RELATED APPLICATIONS

The present application claims the benefit of U.S. provisional patent application 63/067,308 filed Aug. 18, 2020 of like title and inventorship, the teachings and entire contents which are incorporated herein by reference.

BACKGROUND OF THE INVENTION

1. Field of the Invention

The present invention pertains generally to an apparatus and method for measuring ice thickness formed on or near the surface of a body of water. In one specific manifestation, the apparatus comprises a sensor arrangement that indicates ice presence at various distances downward from the surface of the body of water.

2. Description of the Related Art

In the temperate and polar climate zones of the earth, bodies of both fresh and salt water regularly form a layer of ice in the late fall and winter months. Once of sufficient thickness, and therefore strength, this layer of ice is utilized for many recreational and commercial activities. Ice fishing, skating, snowmobiling, and ice sailing are all common recreational ice activities. In extreme example, thick winter ice is also used as a roadway upon which very large and heavy trucks may travel. Knowing the thickness of the ice is essential for determining if the ice is safe for a particular activity, especially early in the winter season when the ice is forming or late in the season as it is thinning.

Some artisans have developed and refined mathematical models that can be used to fairly accurately predict ice thickness. Exemplary publications, the teachings which are incorporated herein by reference, include: ASHTON, "Thin Ice Growth", Water Resources Research, Vol. 25, No. 3, March 1989, Pp. 564-566; LEPPARANTA, "Modelling the Formation and Decay of Lake Ice", The Impact of Climate Change on European Lakes, 2010, Pp. 63-83, Springer Science+Business Media B.V.; and YOSHIKAWA et al, "A simple equation for ice sheet thickness and ice formation/ breakup prediction", Journal of JSCE, Vol. 2, 2014, Pp. 203-213. While these calculations provide good general characterization of the status of an ice sheet, a variety of complicating factors affect local ice formation. Circulating or moving water will thin the ice, as will direct solar radiation, snow, and objects or plant matter that insulate the ice surface from the air. In contrast, very still water, an unobstructed ice surface, and well-shaded areas will thicken the ice. In these and certain other circumstances local ice thickness can vary dramatically from that calculated by a model. Consequently, ice thickness at a specific location can remain elusive using these models, and can in some instances remain dangerously thin even in the depths of winter. In consideration thereof, where safety is important the local ice thickness still needs to be measured and monitored.

There are a number of manual methods that have been devised to determine the thickness of the ice. One common practice is to measure the thickness of ice by boring a hole in the ice and using a measuring tape to determine ice thickness. Measuring aids have also been proposed to better enable this process. In U.S. Pat. No. 4,375,721 by Ueda, entitled "Collapsible restraint for measuring tapes", the teachings which are incorporated herein by reference, a device is disclosed for a collapsible restraint to position a measuring device in an ice hole to determine ice thickness. The obvious disadvantage of boring a hole in the ice is that a person must travel on the ice to the test location to bore the hole and take the measurement. As a result, when the ice turns out to be too thin even to walk on, the person is risking their own safety to venture out onto the ice to measure it. Nevertheless, detection of these unsafe thin ice conditions are often of the most interest. Further, the process of boring disrupts and may weaken already thin and fragile ice. This means that the person might successfully travel to the desired measuring location, but create unsafe ice in the process of taking the ice thickness measurement. Even when the ice is successfully measured using this technique, if the desired measurement location is not in but near to an area where there are currents in the water underneath the ice, the measurement may inaccurately represent the safety of the ice. Consequently, the person must not stop with one hole drilled in the ice, and instead must make more bores, further weakening the ice and endangering the person.

Unattended means to measure ice thickness have been proposed to eliminate the need for an individual to traverse the ice to make a measurement of ice thickness. One class of devices relies on mechanical apparatus for operation. One such method is described in U.S. Pat. No. 4,175,512 by Iwanicki, entitled "Ice thickness indicator", the teachings which are incorporated herein by reference, which discloses a floating buoy of specialized shape that incorporates a mechanism to visually indicate ice thickness. Unfortunately, the apparatus itself insulates the surface of the water from the surrounding air, and so will have ice thickness underneath the Iwanicki apparatus that is very different from the actual surrounding ice thickness. In addition, the entirely mechanical indication provided by the Iwanicki apparatus is extremely difficult to see from a distance at night. In the winter months at northern latitudes, the night can be much longer than the day, and so it may well be dark when a person wishes to know the ice thickness. Similar drawbacks and limitations are found in U.S. Pat. No. 4,426,885 by Visco, entitled "Device for indicating the thickness of ice", the teachings which are also incorporated herein by reference.

A related apparatus that combines mechanical sensing with electrical apparatus is described in U.S. Pat. No. 8,299,931 by Eggleston, entitled "Ice safety device", also published as 2011/0050429, the teachings which are incorporated herein by reference. This apparatus employs a floating buoy with a vertically reciprocating rod that is linked through a cable to a remote-controlled driving motor. The motor moves the rod from an extended position lower position upward until a flange around the base of the rod comes into interference contact with the bottom of the ice sheet. This Eggleston patent incorporates a flag or visual indicator, but does also propose a red and green pair of lights to signal a go or no-go condition. What is desired in embodiments of the present invention is a direct numeric measurement of the ice thickness.

However, the float used by the Eggleston patent suffers from the same drawback as the Iwanicki and Visco apparatuses discussed herein above. The float will drastically alter ice thickness in the immediate vicinity of the buoy, making all readings highly inaccurate. In addition, the moving components of these aforementioned buoys are above the surface of the ice and are highly susceptible to the elements and can freeze up or jam readily.

In fact, and as will be repeated herein below, one of the greatest challenges of most remote or unmanned ice thickness detectors is misdetection of ice thickness resulting from alterations of the boundary-layer ice or water that will form directly on the ice thickness detector. In the case of the open or ice-covered bodies of water to which the present invention pertains, most of the prior art ice thickness detectors alter the ice conditions immediately adjacent to and surrounding the ice thickness detectors. For exemplary and non-limiting purpose, on warm days and days with high solar influx or insolation, the ice thickness detector also heats, leading to the formation of a thin boundary layer of water surrounding the ice thickness detector. As a result, the ice thickness detector reports a complete lack of ice. This can occur even when the ice is of sufficient thickness to be safe for an intended purpose. On extremely cold days, the ice thickness detector may form a boundary layer of ice all the way to the bottom of the ice thickness detector, in this case reporting a very thick and safe ice layer, even when the actual ice thickness may be very thin and unsafe.

Several additional U.S. patents describe reciprocating probes related conceptually to the Eggleston patent, the teachings and content which are incorporated herein by reference, including: U.S. Pat. No. 2,803,813 by Bullen et al, entitled "Device for sensing the formation of solids in a fluid media"; and U.S. Pat. No. 4,873,510 by Khurgin, entitled "Ice detector with movable feeler". These are also very sensitive to boundary conditions between the sensor and surrounding water that, as just explained, can adversely very consequentially change the output from the sensor. Further, and again similarly to the Eggleston patent, these patents provide no protection for the reciprocating probes, meaning they are also easily jammed or otherwise adversely affected by an accumulation of debris, sediments, corrosion, and the like. The Khurgin patent uses a feeler that is projected through an opening to detect the presence of ice. This sensor is designed to project the feeler from inside the housing and out into an airstream, and not a liquid, and would be difficult to seal properly for immersion for long periods, possibly months, in bodies of water. These bodies of water may tend to have a high degree of sediments that will collect on the feeler or inside the feeler cavity and foul its operation. Additionally, the feeler needs to project substantially past the planar surface containing the aperture, as the ice formation might not occur in the boundary layer of liquid at the aperture opening, due to thermal conduction from slightly warmer water below the underside of the ice. An electrical heater is used to actuate the feeler and this requires high electrical power consumption due to intended operation of the device specifically at ambient temperatures that are close to or below freezing. As a result, and undesirably, the Khurgin patent is also unsuitable for long duration battery operation.

To avoid potential binding and jamming of mechanical components, some artisans have devised sealed systems that have one portion inserted into the body of water as a sensor, and which thereby respond to freezing conditions with an increase in volume consumed by the ice relative to the water it was frozen from. A suitable sensor of various type is then used to detect the pressure or volumetric change. Exemplary U.S. patents, the teachings which are incorporated herein by reference, include: U.S. Pat. No. 525,548 by Humberstone, entitled "Frozen water alarm"; U.S. Pat. No. 2,561,437 by Cobb, entitled "Temperature sensitive device for ice bank controllers"; and U.S. Pat. No. 2,622,923 by Cobb, entitled "Ice bank controller". Unfortunately, these probes are also subject to false detection arising from the boundary icing and melting around the sensor. In addition, the manufacture of these types of sensors tends to be costly, and the harsh exposure to the elements can lead to premature failure of the seals.

Another approach is the use of a vertically oriented thermistor string. Each thermistor in the vertical string acts as an elevation-based ice detector, dependent upon detecting a difference in temperature between water and ice. Exemplary published articles, the teachings which are incorporated herein by reference, include: DIBIASIA et al, "Design and Prototype of a Freshwater Ice Thickness Measuring Device", Apr. 25, 2017, 67 pages, Worcester Polytechnic Institute; and POLASHENSKI et al, "Seasonal ice mass-balance buoys: adapting tools to the changing Arctic", Annals of Glaciology 52(57) 2011, pp 18-26. While the approach described in these articles very admirably overcomes the aforementioned limitations regarding binding and jamming of mechanical components, and can provide a low-cost and generally easily manufactured sensor, sensitivity to unrepresentative ice or water formation in the boundary layer of the sensor housing remains an issue.

In addition, thermistor detectors suffer from another serious challenge. The difference in temperature between water and ice is small. Further, both elevation above sea level and variations in contaminants and impurities, including salinity concentration, can exceed this small temperature difference between ice and water. As a result, the thermistor detector must be carefully calibrated for a particular body of water, factoring in both elevation above sea level and the instantaneous effect of impurities. Unfortunately, even with the best of calibration, the thermistor string may be falsely triggered. Transient events such as heavy rain or melting snow cover accompanied by large run-off that carries impurities and flows into the body of water, substantial seasonal evaporation, the well-known turning of a lake just before and as the ice starts to form, and the like can all alter the composition of the water and change the freezing point, negating any previous calibration.

Ice detectors that incorporate electrical sensing elements to determine ice thickness have also been implemented widely. These apparatuses have included resistive, capacitive, and inductive measurements that are used to infer ice thickness. Exemplary U.S. patents, published applications and published articles, the teachings which are incorporated herein by reference, include: U.S. Pat. No. 2,557,311 by Pond, entitled "Ice detector means"; U.S. Pat. No. 2,577,779 by Lindberg, entitled "Icing detection device"; U.S. Pat. No. 2,632,308 by Engelhardt, entitled "Ice detecting system"; U.S. Pat. No. 3,134,563 by Stuetzer, entitled "Ice warning device"; U.S. Pat. No. 3,233,078 by Siemianowski, entitled "Automatic device for preventing ice formation in gutters and downspouts"; U.S. Pat. No. 3,277,459 by Werner, entitled "Conductivity-type ice detector"; U.S. Pat. No. 3,496,733 by Parker et al, entitled "Electronic ice bank control"; U.S. Pat. No. 3,502,899 by Jones, entitled "Liquid level and ice bank control"; U.S. Pat. No. 3,882,381 by Gregory, entitled "System for detecting wet and icy surface conditions"; U.S. Pat. No. 4,287,472 by Pan et al, entitled "Method for measuring the thickness of an ice sheet"; U.S. Pat. No. 4,384,282 by Dennison, Jr., entitled "Device for indicating a freezing temperature in a selected location"; U.S. Pat. No. 4,418,570 by Warren, Jr. et al, entitled "Ice thickness inductor probe"; U.S. Pat. No. 4,497,179 by Iwans, entitled "Ice bank control system for beverage dispenser"; U.S. Pat. No. 4,939,908 by Ewing et al, entitled "Apparatus for adjustably controlling the size of an ice bank"; U.S. Pat. No. 4,996,493 by Monat et al, entitled "Instantaneous ice detection system"; U.S. Pat. No. 5,551,288 by Geraldi et al, entitled "Measuring ice distribution profiles on a surface with attached capacitance electrodes"; U.S. Pat. No. 5,955,887 by Codner et al, entitled "Impedance type ice detector"; U.S. Pat. No. 9,625,248 by Figueroa-Karlstrom, entitled "Device and method for measuring ice thickness"; U.S. Pat. No. 10,066,923 by Go et al, entitled "Ice thickness measurement sensor"; 2015/0260501 by Go et al, entitled "Ice thickness measurement sensor"; "CS616 30 cm Water Content Reflectometer", Product, Jul. 8, 2020, 2 pgs, Campbell Scientific, Inc.; "CS616 and CS625 Water Content Reflectometers", Product Manual, May 2020, 41 pgs, Campbell Scientific, Inc.; REED et al, "Evaluation of Low-Cost, Automated Lake Ice Thickness Measurements", Journal of Atmospheric and Oceanic Technology, April 2019, Pp. 527-34; "Quantifying Ice and Frost Buildup Using Capacitive Sensors", TI TechNotes, SNOA973, December 2017, 3 pages, Texas Instruments Incorporated; and WHITAKER et al, "Lake ice measurements from soil water content reflectometer sensors", Limnol. Oceanogr.: Methods 14, 2016, Pp. 224-230.

There are several issues with electrical-characteristic ice sensors. The physical and electrical properties of water and ice vary widely, especially in freshwater lakes. This makes calibration of such sensors critical and difficult as one would need to know the selected electrical properties of the water prior to installing the sensor. Even subsequent to installation, the selected electrical properties of water can change over the course of days, weeks, or months, destroying any previous calibration. This effect can be particularly pronounced in moving water, rain or melting snow cover that carries impurities and flows into the body of water, and during the turnover of water that occurs as a body of water begins to freeze. Once again, the initial freezing is a time of particular interest, and drifting from initial calibration can render the sensor useless. Many of these electrical-characteristic ice sensors are also susceptible to fouling from an accumulation of surface contaminants that insulate or otherwise alter the electrical characteristics at the interface between sensing element and the fluid being monitored.

In an attempt to overcome the limitations of these types of electrical characteristic sensors, U.S. Pat. No. 5,606,864 by Jones, entitled "Ice bank control for a beverage dispensing machine", the teachings which are incorporated herein by reference, provides a sealed tube prefilled with water of known characteristic, and inserts the tube into the body of water to be measured. While this very creative approach undoubtedly has much application, in the case of the open bodies of water to which the present invention pertains, the sealed tube itself will alter the ice conditions immediately adjacent to and surrounding the sealed tube, as described herein above with respect to other apparatuses. As a result, the formation of ice within the sealed tube is not always accurately representative of the ice covering the water body.

Another class of ice detection sensors has been proposed primarily for the detection of ice on aircraft structures. Included among these are aircraft-type pressure differential icing detectors. Exemplary U.S. patents, the teachings which are incorporated herein by reference, include: U.S. Pat. No. 2,338,574 by Cunningham, entitled "Pressure responsive apparatus for detection or control of ice or for other purposes"; U.S. Pat. No. 2,775,678 by Flubacker, entitled "Ice detecting probe"; U.S. Pat. No. 2,775,679 by Flubacker, entitled "Ice detection system"; U.S. Pat. No. 2,775,680 by Flubacker, entitled "Ice detection system"; U.S. Pat. No. 2,820,958 by Fraser, entitled "Whirling icing detector"; U.S. Pat. No. 2,874,259 by Morris, entitled "Ice detector and control system"; and U.S. Pat. No. 3,123,701 by Padgett, Jr., entitled "Control device responsive to ice-forming conditions".

However beneficial they may be for aircraft and other moving vehicles, these patents lack any teaching for how they would be applied beneficially to buoys anchored within open bodies of water: Similarly, aircraft-type vibratory conduction ice detectors also are configured to provide detection of ice on aircraft and similar moving vehicles based upon measurement of the conduction of vibration from one location to another, such as across a span of an aircraft wing. Exemplary U.S. patents, the teachings which are incorporated herein by reference, include: U.S. Pat. No. 2,419,454 by Le Clair, entitled "Apparatus for detecting and indicating and/or measuring ice formation on vehicles"; U.S. Pat. No. 4,461,178 by Chamuel, entitled "Ultrasonic aircraft ice detector using flexural waves"; and U.S. Pat. No. 4,775,118 by Daniels, entitled "Ice detecting system". These patents explicitly are configured to detect boundary layer conditions, and so are subject to inaccuracy due to the herein above described variability in the boundary layer between sensor and water. They also lack any teaching for how they would be applied beneficially to open bodies of water.

Aircraft vibration detectors are also known that generate a vibration and detect dampening or loading of the vibratory element responsive to aircraft icing. Exemplary U.S. patents, the teachings which are incorporated herein by reference, include: U.S. Pat. No. 2,414,756 by May, entitled "Condition responsive device"; U.S. Pat. No. 2,789,281 by Short et al, entitled "Ice detector"; U.S. Pat. No. 2,800,647 by Baerwald et al, entitled "Ice detector"; U.S. Pat. No. 3,270,330 by Weinberg, entitled "Ice detecting apparatus"; U.S. Pat. No. 3,341,835 by Werner et al, entitled "Ice detector"; U.S. Pat. No. 3,541,540 by Hughes, entitled "Ice detectors"; U.S. Pat. No. 3,706,981 by Hart, entitled "Indicating system for detecting gaseous and non-gaseous states"; U.S. Pat. No. 4,532,806 by Bruchmueller, entitled "Sensor for monitoring the deposition of frozen fog and/or ice on surfaces"; U.S. Pat. No. 4,553,137 by Marxer et al, entitled "Non-intrusive ice detector"; U.S. Pat. No. 4,568,922 by Schwippert et al, entitled "Ice deposition detector employing impedance change of a vibratory body"; U.S. Pat. No. 4,611,492 by Koosmann, entitled "Membrane type non-intrusive ice detector"; U.S. Pat. No. 4,721,949 by Provencal et al, entitled "System for measuring glaze-ice by microprocessor with new release mechanism incorporated"; U.S. Pat. No. 5,187,980 by Blair et al, entitled "Method and apparatus for acoustic plate mode liquid-solid phase transition detection"; and U.S. Pat. No. 5,507,183 by Lame et al, entitled "Ultrasonic method and apparatus for detecting and identifying contamination such as ice on the surface of a structure". Once again, these patents explicitly are configured to detect boundary layer conditions, and so are subject to inaccuracy due to the herein above described variability in the boundary layer between sensor and water. They also lack any teaching for how they would be applied beneficially to open bodies of water.

Yet another class of ice detectors use a radiation transmitter and detector pair to detect ice presence, position, thickness, or the like. Exemplary U.S. patents and publications, the teachings which are incorporated herein by reference, include: U.S. Pat. No. 2,480,846 by Friedman et al, entitled "Ice detector"; U.S. Pat. No. 3,621,714 by Puccinelli, entitled "Ice detector means"; U.S. Pat. No. 3,781,566 by Meuller, entitled "Detecting the presence of a medium in the path of a sound or light wave"; U.S. Pat. No. 3,836,846 by Overall et al, entitled "Ice detection apparatus employing microwave reflectance"; U.S. Pat. No. 3,935,834 by Buhrmann, Jr., entitled "Frost line indicator"; U.S. Pat. No. 4,054,255 by Magenheim, entitled "Microwave ice detector"; U.S. Pat. No. 4,470,123 by Magenheim et al, entitled "Microwave ice accretion meter"; U.S. Pat. No. 4,628,736 by Kirby et al, entitled "Method and apparatus for measurement of ice thickness employing ultra-sonic pulse echo technique"; U.S. Pat. No. 4,646,068 by Skala, entitled "Ice monitoring system using neutron moderation"; U.S. Pat. No. 4,782,331 by Martens, entitled "Photoelectric icing detector"; U.S. Pat. No. 6,049,282 by MacKenzie, entitled "Method and apparatus for measuring ice thickness on substrates using backscattering of gamma rays"; U.S. Pat. No. 6,425,286 by Anderson et al, entitled "Electro-optic ice detection device"; U.S. Pat. No. 8,132,461 by Clasen et al, entitled "Ice thickness measuring system"; and BROWN, "A comparison of simulated and measured lake ice thickness using a Shallow Water Ice Profiler", Hydrol. Process. (2011), 10 Pgs, Wiley Online Library. These ice detection techniques again tend to be generally extremely sensitive to barrier layer icing, contrary to the objective of the present invention, are also generally quite expensive to implement, and tend to consume a substantial amount of power rendering many of them useless for longer term application to an open or ice-covered body of water.

Another class of ice detectors use a rotary shaft detector. Exemplary U.S. patents, the teachings which are incorporated herein by reference, include: U.S. Pat. No. 1,979,546 by Heintz, entitled "Temperature control"; U.S. Pat. No. 2,427,778 by Gregg, entitled "Ice detecting mechanism"; U.S. Pat. No. 2,846,555 by Grieger, entitled "Icing-condition detecting instrument"; U.S. Pat. No. 2,901,741 by Moore et al, entitled "Ice detectors"; U.S. Pat. No. 2,961,842 by Wright, entitled "Mechanical control for ice level in storage bin"; U.S. Pat. No. 3,091,680 by Adrig, entitled "Ice detector"; U.S. Pat. No. 3,350,541 by Richardson, entitled "Icing detector"; and U.S. Pat. No. 4,638,640 by Whetstone et al, entitled "Ice thickness controller for an ice making machine". Where a seal is provided at all, these patents locate the seal above the water to avoid any leakage. The use of such a rotary shaft in a submerged position for extended periods is likely to leak or seep, potentially harming internal components and electronics. Consequently, these fail to provide teachings of how to apply such concepts to open or ice-covered bodies of water.

Patents incorporated herein by reference that teach or illustrate components or concepts the benefits of which have been recognized herein by the present inventor, but which fail to illustrate or teach the combination of features and benefits of the present invention, include: U.S. Pat. No. 2,421,819 by Vandenberg, entitled "Device for regulating the thickness of ice formations on an evaporator coil"; U.S. Pat. No. 2,494,877 by Idrac, entitled "Icing indicator"; U.S. Pat. No. 4,551,982 by Kocher et al, entitled "Ice-thickness sensing device in refrigeration system"; U.S. Pat. No. 5,021,769 by Schuellein, entitled "Ice detector for protecting boats"; U.S. Pat. No. 6,253,557 by Credle, entitled "Ice bank detector"; and U.S. Pat. No. 8,049,522 by Vadder et al, entitled "Ice thickness probe, ice thickness probe assembly and ice thickness monitoring apparatus" also published as 2010/0052703.

Other diverse U.S. patents of varying relevance, the relevant teachings and contents which are incorporated herein by reference, include: U.S. Pat. No. 2,171,450 by Langley, entitled "Means for detecting ice forming conditions, particularly when encountered by aircraft"; U.S. Pat. No. 2,193,836 by Winther, entitled "Air conditioning system for railway cars"; U.S. Pat. No. 2,541,512 by Hahn, entitled "Icing indicator system"; U.S. Pat. No. 2,786,927 by Veldhuis, entitled "Automatic de-icing system"; U.S. Pat. No. 4,175,445 by Templeton III, entitled "Pressure sensing apparatus"; U.S. Pat. No. 5,022,233 by Kirschner et al, entitled "Ice bank control system for beverage dispenser"; U.S. Pat. No. 5,446,448 by Zufelt et al, entitled "River ice motion detector"; U.S. Pat. No. 5,710,554 by Pettler et al, entitled "Pavement ice detector"; U.S. Pat. No. 6,456,197 by Lauritsen et al, entitled "Oil-in-water detector buoy arrangement"; and U.S. Pat. No. 6,758,091 by Nielsen, entitled "Method and an apparatus for measuring icing".

Additional U.S. patents, the teachings which are incorporated herein by reference, illustrating various lights and indicators, include: U.S. Pat. No. 332,480 by Boyle, entitled "Magneto electric indicator"; U.S. Pat. No. 354,508 by Fraleigh, entitled "Indicator for reservoirs"; U.S. Pat. No. 459,323 by Weuste, entitled "Electric contact apparatus"; U.S. Pat. No. 532,868 by Bull, entitled "Electrical annunciator"; U.S. Pat. No. 712,699 by May, entitled "Means for ascertaining the level of liquids"; U.S. Pat. No. 954,727 by Fryett et al, entitled "Hydraulic indicator"; U.S. Pat. No. 1,079,229 by Fitzgerald, entitled "Electrically controlled indicator"; U.S. Pat. No. 1,081,843 by Larson, entitled "Indicator"; U.S. Pat. No. 1,139,489 by Church, entitled "Indicator"; U.S. Pat. No. 1,154,162 by Baker, entitled "Signal apparatus"; U.S. Pat. No. 1,162,699 by Kline, Jr., entitled "Device for indicating liquid levels at a distance"; U.S. Pat. No. 1,175,417 by Fehrenbach et al, entitled "Electric meter and fluid gage"; U.S. Pat. No. 1,179,486 by Wight, entitled "Water level recorder"; U.S. Pat. No. 1,224,741 by Hewis, entitled "Indicator for fluid containers"; U.S. Pat. No. 1,278,949 by Le Compte, entitled "Liquid level gage"; U.S. Pat. No. 1,347,944 by Gervasoni et al, entitled "Apparatus for indicating the level of liquids at distance"; U.S. Pat. No. 1,414,298 by Montero, entitled "Indicator"; U.S. Pat. No. 1,435,411 by Mitchell, entitled "Float operated circuit closer"; U.S. Pat. No. 1,634,165 by Williams, entitled "Electric gasoline gauge"; U.S. Pat. No. 1,678,115 by Hanon, entitled "Gasoline gauge"; U.S. Pat. No. 2,203,766 by Baer et al, entitled "Measuring instrument"; U.S. Pat. No. 2,210,775 by Perry, entitled "Electrical switch"; U.S. Pat. No. 2,216,069 by Doyle, entitled "Telemetric system for remote indication"; U.S. Pat. No. 2,902,669 by Lucarelli, entitled "Highway guard"; U.S. Pat. No. 3,002,186 by Schlangen, entitled "Oil gauge"; U.S. Pat. No. 3,320,805 by Kahle, entitled "Data collection system"; U.S. Pat. No. 3,484,774 by Borgnakke, entitled "Magnetically actuated liquid level indicator"; U.S. Pat. No. 3,523,456 by Matzen et al, entitled "Liquid level indicator for a dispenser"; U.S. Pat. No. 3,545,272 by McGill, entitled "Liquid level warning device"; U.S. Pat. No. 3,614,759 by Moore et al, entitled "Indicating apparatuS"; U.S. Pat. No. 3,685,357 by Alexander, entitled "Sensor responsive to liquid level"; U.S. Pat. No. 3,992,941 by McGoldrick, entitled "Liquid level measuring apparatus"; U.S. Pat. No. 4,086,812 by Luthe et al, entitled "Display device"; U.S. Pat. No. 4,125,022 by Sumida, entitled "Digital fuel quantity indicators"; U.S. Pat. No. 4,175,435 by Hara, entitled "Liquid level detecting device"; U.S. Pat. No. 4,250,750 by Martinec et al, entitled "Liquid level measuring system"; U.S. Pat. No. 4,303,984 by Houvig, entitled "Sensor output correction circuit"; U.S. Pat. No. 4,361,039 by van der Lely, entitled "Tank for transporting liquid material"; U.S. Pat. No. 4,459,584 by Clarkson, entitled "Automatic liquid level indicator and alarm system"; U.S. Pat. No. 4,571,998 by Stegner, entitled "In-ground tank measuring system"; U.S. Pat. No. 4,730, 491 by Lew, entitled "Magnetically activated multiple switch level detector"; U.S. Pat. No. 5,079,950 by McKiernan et al, entitled "Level indicating in vehicle holding tanks"; U.S. Pat. No. 5,103,673 by Sawada et al, entitled "Fluid level indicator for small watercraft"; U.S. Pat. No. 5,134,380 by Jonas, entitled "Icing detector and method"; U.S. Pat. No. 5,483,831 by Steiner, entitled "Direct liquid level reading device"; U.S. Pat. No. 6,370,952 by Little et al, entitled "Vehicle oil level monitoring system"; U.S. Pat. No. 6,532,814 by Bromley, entitled "Apparatus and method for detecting a leak in a swimming pool"; U.S. Pat. No. 7,423,541 by Miller, entitled "Excessive product usage detection using a level monitoring system"; U.S. Pat. No. 7,617,725 by Howayshell, entitled "Electric generator protection system"; and U.S. Pat. No. 8,171,786 by Burris, entitled "Fuel inventory monitoring system".

As may be apparent, in spite of the enormous advancements and substantial research and development that has been conducted, there still remains a need for an ice thickness transducer that is substantially insensitive to boundary layer conditions between the transducer and body of water, which accurately detects the actual ice thickness of the body of water, and which can remain operative in the body of water for weeks or months.

In addition to the foregoing patents and publications, Webster's New Universal Unabridged Dictionary, Second Edition copyright 1983, is incorporated herein by reference in entirety for the definitions of words and terms used herein.

SUMMARY OF THE INVENTION

In accord with the teachings of the present invention, an ice thickness transducer projects down from the surface of a body of water. A plurality of ice presence sensors are placed at points of increasing depth along the body of the ice thickness transducer, each which determine if water or ice is present at that depth. As the body of water freezes, it freezes downward, covering an increasing number of the ice presence sensors. By knowing which ice presence sensors are covered with ice, the thickness of the ice can be determined with a measurement span determined by the overall distance from the top surface of the water/ice to the furthest ice presence sensor from the surface. The resolution, or minimum span between different ice thicknesses that can be detected, is determined by the number of ice presence sensors employed.

A preferred embodiment ice thickness transducer is comprised of several main components, including a sense probe, actuator assembly, and a switch. The sense probe is coupled to an actuator assembly internal to the transducer through a flexible watertight membrane. A preferred embodiment actuator assembly has a combination of rigid and flexible components to move the probe and change the state of a switch that is in contact with the actuator assembly. If the sense probe is immersed in liquid water, the actuator assembly will be able to move the sense probe and it will change the state of the switch. If the sense probe is immersed in ice, the actuator assembly will not be able to move the sense probe and it will not change the state of the switch. It is this difference in behavior that is measured. A transducer housing provides the enclosure and support for one or more ice presence sensors. The transducer housing has holes in it over its length to provide installation and operation of ice presence sensors for the desired measurement span and resolution. The transducer housing also provides means to position it in a body of water such that it floats and remains in the location where the ice thickness measurement is desired. A controller provides means to periodically energize the actuators as part of the ice presence sensors and to read the state of the switches in the one or more ice presence sensors. The controller determines whether ice is present at each of the ice presence sensors, calculates the ice thickness responsive to this determination, and outputs these values for display and communication.

A preferred embodiment ice thickness transducer may have one or more visual displays that present ice thickness. Unlike previous implementations that only have a mechanical display that would be difficult to see in poor conditions or at night, a preferred embodiment ice thickness transducer described herein incorporates a visible indicator that flashes ice thickness. In one exemplary embodiment, the ice thickness transducer is provided with four visible indicators positioned above the surface of the body of water and ice. These visible indicators are preferably light emitting and of sufficient brightness to be seen day or night. The visible indicators are positioned at 90 degree increments to each adjacent visible indicator to allow visibility from any position around the ice thickness transducer. The visible indicator will flash a number of times sequentially with a flash count correlating to the ice thickness. Continuing for exemplary purpose only, and not solely limiting the present invention thereto, for an ice thickness transducer with twelve ice presence transducers spaced one inch apart and seven ice presence sensors detecting ice, the visible indicator would flash seven times sequentially and then wait a short period and repeat to indicate to an observer that the ice thickness transducer is measuring seven inches of ice at that location. In another example, an ice thickness transducer with eight ice presence transducers spaced two inches apart and five ice presence sensors detecting ice would flash ten times sequentially and then wait a short period and repeat to indicate to an observer that the ice thickness transducer is measuring ten inches of ice at that location. The visible display is most preferably sufficiently luminous to be observed at sufficient distance and especially at night to know the measured ice thickness without having to get close to the measurement location. In some embodiments, the ice thickness transducer controller will also interface with a communication module that wirelessly provides the desired indication of ice thickness to a remote receiver such as a mobile device or to a remote server via the internet. In some embodiments, the ice thickness indication will be further processed for logging or analysis.

In a first manifestation, the invention is an ice thickness transducer suspended adjacent a surface of a body of water. A transducer body provides an exterior wall, an interior space, and defines a generally vertical longitudinal axis. A power source provides operational energy. A buoy is coupled to the transducer body and configured to locate the transducer body adjacent the surface of the body of water. At least one ice presence sensor protrudes from the transducer body beyond a boundary layer between the ice thickness transducer and water body and is configured to detect a presence of ice adjacent to the transducer body and beyond the boundary layer. A control unit is coupled to the at least one ice presence sensor and is configured to infer an ice thickness responsive to a detection of a presence of ice by the at least one ice presence sensor.

In a second manifestation, the invention is an ice presence sensor monitors a liquid-solid phase-changing fluid. The ice presence sensor has a sense probe protruding into the liquid-solid phase-changing fluid; a flexible waterproof membrane; an actuator assembly generating a motive force urging the sense probe to move in the liquid-solid phase-changing fluid; and a detector assembly configured to monitor movement of the sense probe responsive to the actuator assembly motive force generation and configured if the sense probe is immersed in liquid to provide a liquid-indicative output and if the sense probe is immersed in ice to provide an ice-indicative output.

In a third manifestation, the invention is an ice thickness transducer that measures an ice thickness and visually displays the measured ice thickness. The ice thickness transducer has a visual display assembly having at least one illuminator; and a control circuit configured to flash the at least one illuminator periodically with a number of flashes within a single period correlated to the measured ice thickness.

OBJECTS OF THE INVENTION

The present invention and the preferred and alternative embodiments have been developed with a number of objectives in mind. While not all of these objectives are found in every embodiment, these objectives nevertheless provide a sense of the general intent and the many possible benefits that are available from embodiments of the present invention.

The primary objective of the present invention is to provide an ice thickness transducer that can measure ice thickness reliably and that can be produced at low cost to enable economical deployment on bodies of water to provide the indication necessary to determine if ice thickness is safe for an intended use. It is a further objective of the present invention to minimize the electrical power required for operation, to enable unattended operation for long durations without maintenance. Additionally the ice thickness transducer is conceived for reliable operation without complicated set-up or calibration in water, liquid or frozen, which may contain a wide variety of contaminants or impurities. An additional objective of the present invention is to provide an ice thickness transducer that is insensitive to icing or thawing conditions within the boundary layer between ice thickness transducer and water body, and instead accurately detects bulk ice thickness spaced from the surface of the ice thickness transducer housing. Yet another objective of the present invention is to incorporate minimal movement of the sense probe adjacent the surface of the ice thickness transducer housing, such that with proper design preferred embodiments of the present invention will function effectively even when a thin boundary layer of ice forms around the outer surface of the ice thickness transducer housing. Another objective of the present invention is to provide both a float geometry and an ice thickness transducer geometry that leave the vast majority of the open or ice-covered water body adjacent the ice thickness transducer uncovered by any components of the ice thickness transducer, so as to either not or only nominally interfere with the normal formation of ice in the area adjacent to the transducer.

BRIEF DESCRIPTION OF THE DRAWINGS

The foregoing and other objects, advantages, and novel features of the present invention can be understood and appreciated by reference to the following detailed description of the invention, taken in conjunction with the accompanying drawings, in which:

FIGS. 1a-1e show a first preferred embodiment ice presence sensor designed in accord with the teachings of the present invention and mounted within an ice thickness transducer, illustrating essential components by enlarged partial cross-section view, and with three views illustrating the operation of the ice presence sensor. FIG. 1a shows the first preferred embodiment ice presence sensor in an unactuated state, with the sense probe protruding from the ice thickness transducer housing into a fluid. FIG. 1B shows the first preferred embodiment ice presence sensor of FIG. 1a when actuated. FIG. 1c shows the first preferred embodiment ice presence sensor actuated, but in this case with the sense probe protruding from the ice thickness transducer housing into ice. FIG. 1d shows a preferred embodiment of coupler 107 and strike plate 108. FIG. 1e shows the first preferred embodiment ice presence sensor from an exterior projected view.

FIGS. 2a-2g show an alternative embodiment ice presence sensor designed in accord with the teachings of the present invention and mounted within an ice thickness transducer, illustrating essential components by enlarged partial cross-section view, and with three views illustrating the operation of the alternative embodiment ice presence sensor. FIG. 2a shows the alternative embodiment ice presence sensor in an unactuated state, with the sense probe protruding from the ice thickness transducer housing into a fluid. FIG. 2b shows the alternative embodiment ice presence sensor of FIG. 2a when actuated. FIG. 2c shows the alternative embodiment ice presence sensor actuated, but in this case with the sense probe protruding from the ice thickness transducer housing into ice. FIG. 2d shows the orientation of the transversely extending arm relative to sense probe of FIG. 2a, taken as a right side view from FIG. 2a of just those two components. FIG. 2e shows the orientation of the transversely extending arm relative to sense probe of FIG. 2b, taken as a right side view from FIG. 2b of just those two components. FIG. 2f shows the orientation of the transversely extending arm relative to sense probe of FIG. 2c, taken as a right side view from FIG. 2c of just those two components. FIG. 2g illustrates a projected view of the alternative embodiment ice presence sensor.

FIG. 7 shows an exemplary ice thickness transducer display driver by block diagram.

FIG. 8 shows an exemplary timing diagram of the preferred embodiment ice thickness transducer display driver of FIG. 7.

FIG. 9 shows an exemplary ice thickness transducer power supply by schematic diagram.

DESCRIPTION OF THE PREFERRED EMBODIMENT

Figure 3:
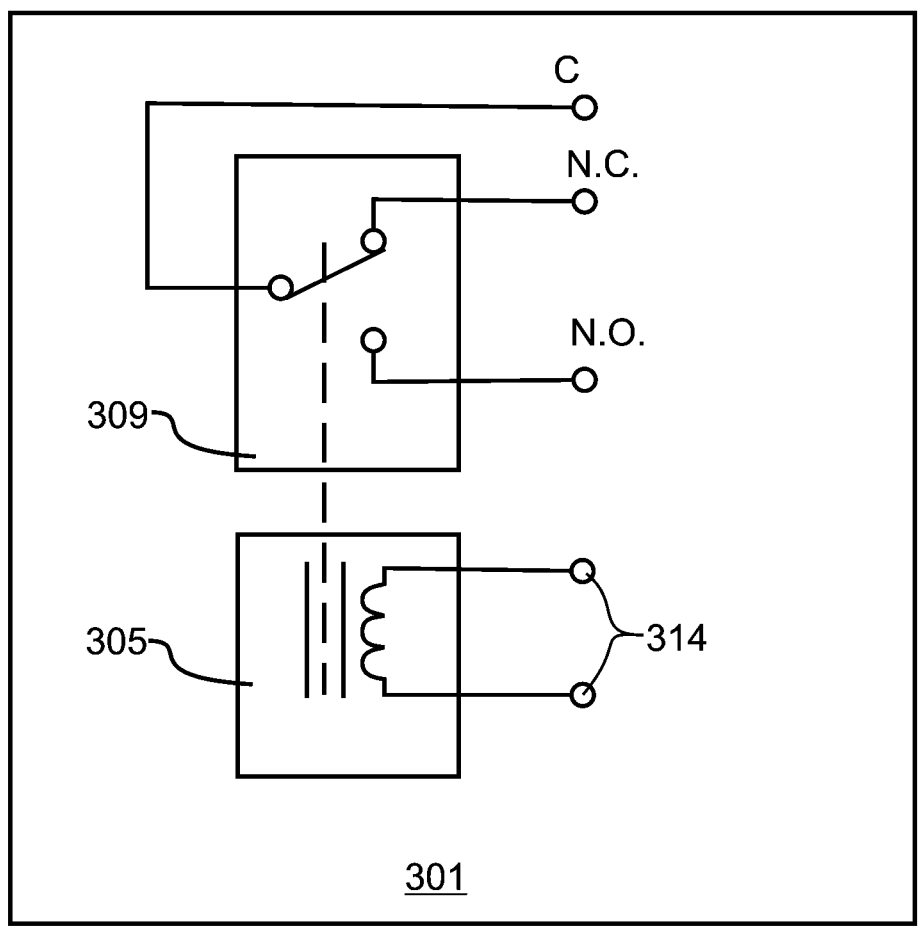
FIG. 3 shows the ice presence sensor schematically.

This description of the exemplary embodiments is non-limiting and is intended to be read in connection with the accompanying drawings, which are to be considered part of the entire written description. It is noted that the drawings may not be to scale. The drawings are intended to depict only typical aspects of the disclosure and therefor should not be considered as limiting the scope of the disclosure. Further, while this description of the preferred embodiment describes application for measuring the thickness of ice over a body of water, the present invention may be applied to measurement of the thickness of many diverse solidified liquids, subsequent to an understanding of the present disclosure.

A preferred embodiment ice thickness transducer designed in accord with the teachings of the present invention relies on the ability to make point determinations of the presence or absence of ice at a particular location adjacent to the immersed transducer body. The distribution of more than one of these point determinations through a depth range enables a determination of the thickness of the ice. The preferred embodiment ice presence sensor provides a means to make a point measurement of the presence or absence of ice proximal to the ice thickness transducer body, regardless of whether the boundary layer of water in contact with the ice thickness transducer body is in a liquid or solid phase.

In accord with the teachings of the present invention, a preferred embodiment ice presence sensor 100 is illustrated in FIGS. 1a-1e. A sense probe 101 is supported by a flexible membrane 103 and probe seals 102 and is immersed in a fluid media 110. In a most preferred embodiment, the fluid media 110 is water of any purity or level of contamination such as may be found for exemplary and non-limiting purpose in a lake, river, or other body of water. Nevertheless, in other alternative embodiments fluid media 110 may be another fluid capable of forming a solid layer and having a liquid adjacent thereto.

Probe seals 102 provide a support for sense probe 101, while also sealing sense probe 101 to membrane 103 to prevent fluid media 110 from passing through. Sense probe 101, probe seals 102, and membrane 103 may each comprise a variety of materials, with preferred materials being ones that will withstand extended contact with and not degrade in fluid media 110 or with the incidence of frozen media 112 surrounding sense probe 101. Sense probe 101 may comprise a variety of geometries, with the preferred embodiment being a shape that extends sense probe 101 into fluid media 110 sufficiently such that when sense probe 101 is surrounded by frozen media 112 it is held rigidly. As may be appreciated, this geometry may change not only by preference of a designer, but also based upon the composition and viscosity of fluid media 110. A preferred material for membrane 103 is also sufficiently flexible and resilient to allow sense probe 101 to move both back and forth or rotate about the axis formed by the intersection of the sense probe 101 with membrane 103 supported and sealed with probe seals 102.

In preferred embodiment ice presence sensor 100, membrane 103 is attached to transducer housing 104, which provides a support for membrane 103 and a liquid tight seal that keeps fluid media 110 external to transducer housing 104. A membrane support flange 113 is optionally but preferably incorporated to provide additional sealing and support for membrane 103. With further reference to FIG. 1a, sense probe 101 extends into the interior cavity formed by transducer housing 104 and is connected to an actuator 105 with return spring 106 by means of a coupler 107. In preferred embodiment ice presence sensor 100, sense probe 101 is loosely held by coupler 107 and is free to move. A strike plate 108 is attached to coupler 107. A preferred embodiment of coupler 107 and strike plate 108 is illustrated in FIG. 1d. A switch 109 is positioned in proximity to and preferably actuated by strike plate 108.

Actuator 105 can be any device that can either directly or through appropriate coupling selectively move sense probe 101 when sense probe 101 distal to actuator 105 is immersed in fluid media 110, but which will not consequentially move or damage sense probe 101 when immersed in frozen media 112. In preferred embodiment ice presence sensor 100, actuator 105 is an electromagnet solenoid energized by flowing electrical current through actuator lead wires 114. In some alternative embodiments, actuator 105 comprises a piezoelectric actuator, while in other embodiments actuator 105 comprises a voice coil actuator similar to that found on a loudspeaker. In further alternative embodiments, a rotary electric motor is combined with a rack and pinion gear to generate motion within sense probe 101. Further, in some embodiments the motion may be vibratory or reciprocating rather than the rotation illustrated in preferred embodiment ice presence sensor 100. Actuator 105 is preferably selected to generate movement complementary with switch 109 or other suitable detector or sensor of the movement of sense probe 101 that is selected by a designer for use within the preferred and alternative embodiments of the present invention.

Switch 109 can be any suitable device that can detectably change state when it senses movement of sense probe 101, such as Hall effect, optical means, capacitive means, or mechanical means, with a preferred embodiment being an electromechanical device that changes the electrical state of switch contacts upon sufficient physical movement of a switch actuator, hereinafter referred to as a switch plunger. In FIG. 1a, strike plate 108 moves with coupler 107, and in the process contacts the switch plunger and thereby changes the electrical state of switch contacts within switch 109. When the plunger of switch 109 is not pressed, there is a low-resistance electrical circuit formed between switch 109 lead C and lead N.C., and a very high-resistance or open circuit between lead C and lead N.O. When the plunger of switch 109 is pressed there is a very high-resistance or open circuit between lead C and lead N.C., and a low-resistance electrical circuit formed between lead C and lead N.O.

The operation of the ice presence sensor 100 is illustrated by the differences between FIGS. 1a-1c. In FIG. 1a, sense probe 101 is immersed in a fluid media 110 and free to move. With actuator 105 not energized, return spring 106 is not compressed, and strike plate 108 connected to the coupler 107 is not actuating switch 109. Referring to FIG. 1b, actuator 105 is energized to compress return spring 106 and apply force to sense probe 101 through coupler 107, causing sense probe 101 to rotate about the axis formed by the intersection of sense probe 101 and membrane 103. While as illustrated in FIG. 1b this axis of rotation is a horizontal axis, roughly parallel to the surface of the water, this axis of rotation may be of any suitable angle, and so in some embodiments will for exemplary and non-limiting purpose comprise a vertical axis or other axis intermediate between horizontal and vertical.

Sense probe 101 is able to rotate since outside of transducer housing 104 it is immersed in liquid water 111, or other suitable fluid media such as fluid media 110. The rotating action of sense probe 101 causes strike plate 108 to push the switch 109 plunger. As a result, switch 109 is caused to change state, breaking the electrical circuit between switch 109 terminals C and N.C. and creating an electrical circuit between terminals C and N.O. When actuator 105 is de-energized, return spring 106 pushes sense probe 101, via coupler 107, back to its original position shown in FIG. 1a. The strike plate 108 moves back to its original position shown in FIG. 1a and switch 109 changes state and now breaks the electrical circuit formed between switch 109 terminals C and N.O. and completes an electrical circuit between switch terminals C and N.C.

In contrast to FIG. 1b, FIG. 1c illustrates when sense probe 101 is encased in ice or other frozen media 112.

Actuator 105 is energized to apply force to the sense probe 101 via coupler 107. Instead of compressing return spring 106, sense probe 101 is not able to rotate since it is immersed in frozen media 112, such as ice. Since sense probe 101 does not rotate, strike plate 108 does not come in contact with switch 109, and switch 109 does not change state. As a result, the electrical circuit between the switch 109 terminals C and N.C. is maintained, even when actuator 105 is energized.

The operation described in the proceeding paragraphs describes how preferred embodiment ice presence sensor 100 works. When actuator 105 is energized and applies a force to sense probe 101, the state of switch 109 changes when sense probe 101 is immersed in a fluid media 110 such as water 111 as shown in FIG. 1b, or instead stays the same when immersed in a frozen media 112 such as ice as shown in FIG. 1c. The state of the switch is sampled by the control electronics and is subsequently used for ice thickness calculation.

Various embodiments of apparatus designed in accord with the present invention have been illustrated in the various Figures, especially FIGS. 1a-1e, 2a-2g, and 4. The embodiments are distinguished by the hundreds digit, and various components within each embodiment designated by the ones and tens digits. However, many of the components are alike or similar between embodiments, so numbering of the ones and tens digits have been maintained wherever possible, such that identical, like or similar functions may more readily be identified between the embodiments. If not otherwise expressed, those skilled in the art will readily recognize the similarities and understand that in many cases like numbered ones and tens digit components may be substituted from one embodiment to another in accord with the present teachings, except where such substitution would otherwise destroy operation of the embodiment. Consequently, those skilled in the art will readily determine the function and operation of many of the components illustrated herein without unnecessary additional description.

An alternative embodiment ice presence sensor 200 is shown in FIGS. 2a-2g, with a projected view provided in FIG. 2g. Referring to FIG. 2a, a sense probe 201 is supported by a flexible membrane 203 and probe seals 202, and is immersed in a fluid media 110. In this alternative embodiment ice presence sensor 200, sense probe 201 defines a longitudinal axis about which sense probe 201 is configured to rotate. This is in contrast to preferred embodiment ice sensor 100 that pivots about an axis parallel to probe seal 102.

Sense probe 201 can be any shape, but in various embodiments illustrated herein comprises a shape that extends sense probe 201 into fluid media 110 sufficiently such that when sense probe 201 is surrounded by frozen media 112 it is held rigidly. As illustrated in FIGS. 2a-2f, sense probe 201 terminates with a transversely extending arm 201a. As illustrated, transversely extending arm 201a is approximately centered on sense probe 201, which provides balanced load on probe seals 202. In alternative embodiments, transversely extending arm 201a will extend unidirectionally from sense probe 201 so as to define an "L" shape therewith, and in yet other alternative embodiments other shapes suitably chosen by a designer at design time will be used. Membrane 203 may comprise a variety of materials, with a preferred material being one that is compatible with fluid media 110 and is sufficiently flexible to allow sense probe 201 to rotate about the longitudinal axis while still providing a secure and leak-proof seal therewith. In this alternative embodiment, membrane 203 is also attached to, supported by, and forms a liquid tight seal with transducer housing 204. Membrane support flange 213, which may comprise any suitable type of fastener(s), provides a seal between membrane 203 and transducer housing 204.

With further reference to FIG. 2a, sense probe 201 extends into the interior cavity formed by transducer housing 204 and is supported by bushing 207. Sense probe 201 is free to rotate in bushing 207. Sense probe 201 at the end distal to arm 201a is attached to actuator 205 via coupler 215. Coupler 215 will convert the linear motion of actuator 205 to rotary motion within sense probe 201. Attached to coupler 215 is a strike plate 208.

Actuator 205 can be any device that can provides linear motion to coupler 215 upon suitable command, activation, or energization, with a preferred embodiment being a solenoid energized by flowing electrical current through actuator lead wires 214. As visible in FIGS. 2a and 2d, when actuator 205 is not energized, return spring 206 orients transversely extending arm 201a in a generally vertical direction.

When actuator 205 is energized via lead wires 214, actuator 205 will pull plunger 216 in and compress return spring 206. This movement in turn pulls coupler 215, such as illustrated in FIGS. 2b and 2e, in turn pulling on sense probe 201 and thereby causing sense probe 201 to rotate within bushing 207. Sense probe 201 flexes membrane 203 and is also rotating within fluid media 110, with transversely extending arm 201a rotating into the position illustrated in FIG. 2e. Flexible membrane 203 allows sense probe 201 to rotate, while the probe seals 202 maintain a liquid tight seal. Since the end of sense probe 201 external to membrane 203 is immersed in fluid 110, it is free to rotate, and thus strike plate 208 connected to coupler 215 moves. Switch 209 is positioned in proximity to strike plate 208. Movement of strike plate 208 actuates switch 209. Switch 209 preferably comprises any suitable device that can detectably state change when sense probe 201 moves, such as hall effect, optical means, capacitive means, or mechanical means, with a preferred embodiment being an electromechanical device that changes the electrical state of switch contacts upon sufficient physical movement of strike plate 208. When switch 209 is not actuated by strike plate 208, there is an electrical circuit formed between switch 209 lead C and lead N.C. Strike plate 208 and coupler 215 may be fabricated from a wide range of materials with suitable rigidity.

This rotational motion of sense probe 201 causes strike plate 208 to come in contact with and move the plunger of switch 209. Switch 209 is thereby caused to change state, breaking the electrical circuit between switch 209 terminals C and N.C. and creating an electrical circuit between terminals C and N.O. When actuator 205 is subsequently de-energized, return spring 206 pushes plunger 216 and coupler 215 attached to sense probe 201 back to the original position shown in FIG. 2a. Strike plate 208 moves back to its original position shown in FIG. 2a and switch 209 changes state and now breaks the electrical circuit formed between switch 209 terminals C and N.O. and completes an electrical circuit between switch terminals C and N.C. The sequence above describes the operation of the ice thickness transducer 200 determining the presence of liquid surrounding the space around sense probe 201.

Referring to FIG. 2c, actuator 205 is energized via lead wires 214 to attempt to pull the plunger 216 into the actuator and compress return spring 206. This will also apply force to coupler 215, which couples the force to sense probe 201 and attempts to rotate it through bushing 207. However, in FIG. 2c sense probe 201 is not able to move since it is immersed in a frozen media 112 such as solidified liquid or ice. Since sense probe 201 does not move, strike plate 208 does not come in contact with switch 209, and switch 209 does not change state, so the electrical circuit between the switch 209 terminals C and N.C. is maintained.

The operation described in the proceeding paragraphs describes how this alternative embodiment ice presence sensor 200 works; switch 209 is able to detect whether sense probe 201 is immersed in a fluid media 110 or frozen media 112 when an actuation force is applied to the sense probe.

The length and geometry of both sense probe 201 and transversely extending arm 201a can be varied to suit a particular goal or objective. Since sense probe 201 rotates about a longitudinal axis, any boundary layer ice that may form thereon and that is misrepresentative of actual water body ice thickness will not materially interfere with such rotation, provided sufficient force is generated by actuator 205 and adequately coupled and maintained through to sense probe 201. In other words, the lever arm and therefore the torque created by the actuator end of sense probe 201 is much larger than the diameter of the longitudinal shaft of sense probe 201. This means that any resistance from ice tending to bind sense probe 201 to transducer housing 204 will face disproportionate and greater torque from actuator 205, and so sense probe 201 is configured to break free from any such boundary ice.

Most preferably, transversely extending arm 201a is located sufficiently distal to transducer housing 204 to be removed from any boundary ice formation, and instead extends fully into the open or ice-covered water body. The length of transversely extending arm 201a will determine how far vertically transversely extending arm 201a will reach when actuator 205 is energized, in turn defining how large an interval of vertical displacement will be checked by sense probe 201 for ice for a given degree of rotation. This capability, as evident from FIG. 4, enables a plurality of sense probes 201 to incrementally check for ice 112 through a substantial range while requiring only a few sets of sense probes 201. When a larger transversely extending arm 201a is used, less rotation is required to cover a vertical displacement range, thereby reducing the deformation in flexible membrane 203 needed to accommodate that same vertical displacement range.

FIG. 3 presents one embodiment of the electrical schematic for an ice presence sense probe 301 designed in accord with the teachings of the present invention. A sense probe movement detector 309 of any suitable type, illustrated herein for exemplary and non-limiting purpose as switch, changes state when sense probe movement detector 309 moves through a sufficient actuating motion initiated by an actuator 305. Actuator 305 may be of any suitable type, illustrated herein for exemplary and non-limiting purpose as an electromagnetic solenoid. If sense probe movement detector 309 is switched as a result of actuation of actuator 305, an electrical circuit is completed between the contacts labeled C (Common) and N.O. (Normally Open) of sense probe movement detector 309. This circuit would indicate to a suitable monitoring apparatus that water or other fluid media 110 is present adjacent to the exposed portion of ice presence sense probe 301. If ice presence sense probe 301 is acted upon by actuator 305 and does not move, an electrical circuit remains instead completed between the contacts labeled C and N.C. (Normally Closed) of switch 309. This circuit indicates to a suitable monitoring apparatus that ice or other frozen media 112 is present at the exposed portion of ice presence sense probe 301. The logic of the switch operation in the proceeding description may be changed if it is convenient to do so for the monitoring apparatus. It is evident to a person with skill in the art that alternative embodiments using other switching and movement or position sensing technologies known in the measuring and testing arts could be used to sense the motion of ice presence sense probe 301 and such switch alternatives and equivalents are considered to be incorporated herein. These technologies include but are not limited to optical switches, magnetic switches, capacitive, impedance, inductive, optical, and magnetic sensors and the like.

Figure 4:
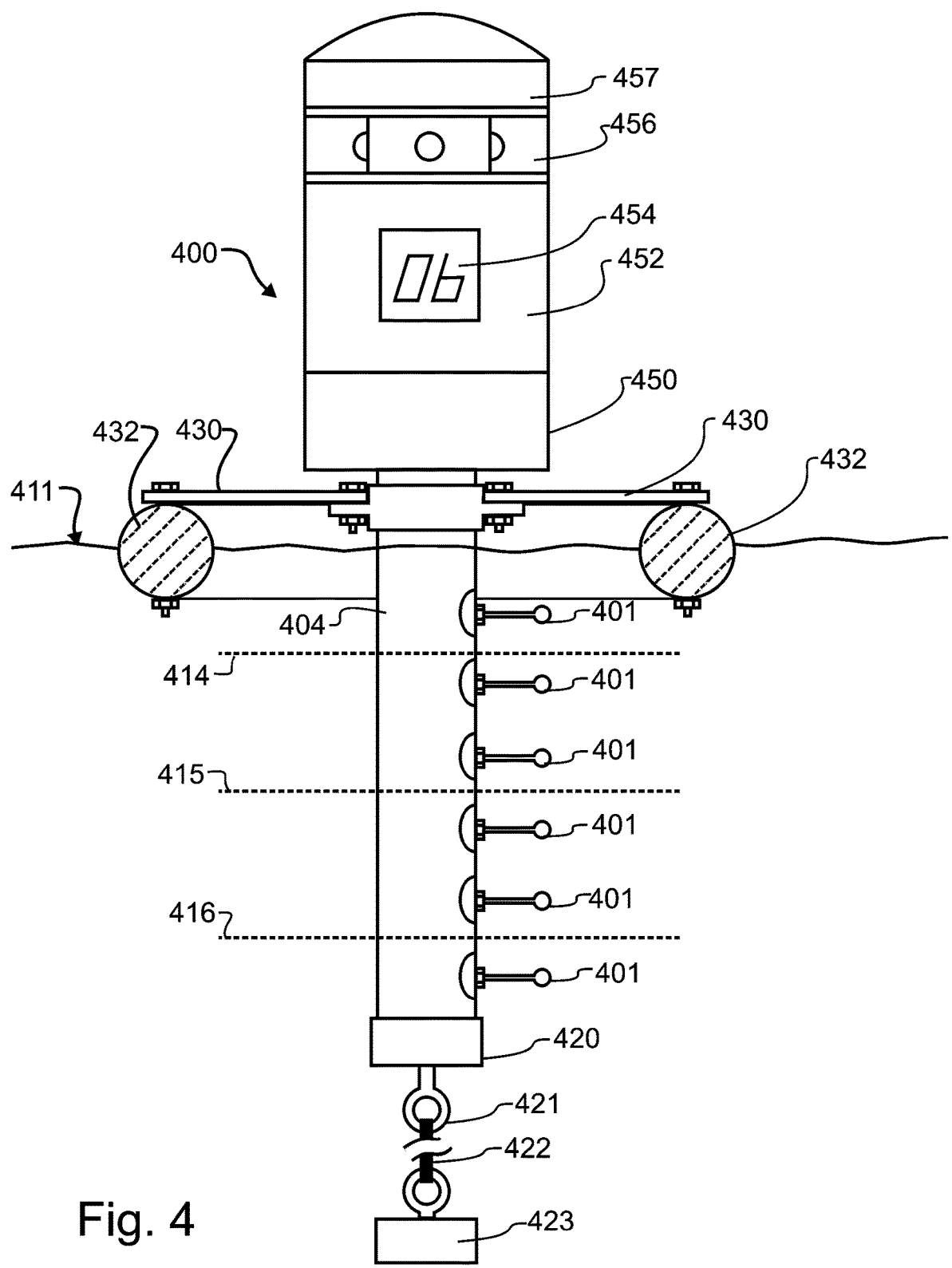
FIG. 4 shows a preferred embodiment ice thickness transducer designed in accord with the teachings of the present invention.

A preferred embodiment ice thickness transducer 400 designed in accord with the teachings of the present invention is illustrated in FIG. 4, immersed in water 411 to provide monitoring of the presence or absence of ice at various meaningful or significant distances from a surface of the body of water 411. Preferred embodiment ice thickness transducer 400 contains and suitably positions at least one and in many embodiments a plurality of ice presence sensor probes 401, which might for exemplary and non-limiting purpose protrude from one of preferred or alternative embodiment ice presence sensors 100, 200 relative to the surface of the body of water 411. Each one of any ice presence sensor probes 401 determines a presence or absence of ice 112 at the depth of the particular ice presence sensor probe 401 below the surface of the body of water 411.

When only one ice presence sensor probe 401 is provided, preferred embodiment ice thickness transducer 400 will preferably detect and signal when ice reaches the depth of the single ice presence sensor probe 401. This can be useful when a person only needs to know whether the ice has reached an adequate or sufficient depth required for a particular purpose. Nevertheless, for many applications a person will prefer to know that the ice thickness has crossed not only one threshold, but several. So, for exemplary and non-limiting purpose, when ice is of a first minimal thickness, the person may ski or ride a lower weight ATV with larger tires upon it safely. As the ice thickens to a second threshold, the person may then walk safely upon the ice, and at a third threshold, the person may drive a snowmobile. As may be appreciated, each of these ice thickness thresholds, or others to be determined by a designer in light of the teachings of the present disclosure, are meaningful and important to a person. In such cases, a plurality of ice presence sensor probes 401 are placed at suitable locations longitudinally along transducer housing 404. In some embodiments, the locations selected for ice presence sensor probes 401 are specifically at particular thicknesses associated with a purpose. In other embodiments, ice presence sensor probes 401 are instead placed at equidistant locations along transducer housing 404.

Since it is well known that ice formation begins at the water surface and proceeds downward therefrom, an ice presence sensor probe 401 will detect the presence of ice at that position on the transducer body as the ice forms from the surface of a body of water 411 thereto. Referring to FIG. 4, and for exemplary purpose only not limiting the present invention solely thereto, if the thickness of the ice has reached a depth indicated by reference numeral 414, the ice presence sensor probe 401 nearest the surface will indicate the presence of ice. If the thickness of the ice has reached the depth indicated by 415 then the three ice presence sensor probes 401 nearest the surface will indicate the presence of ice. If the thickness of the ice has reached the depth indicated by 416 then the five ice presence sensor probes 401 nearest the surface will indicate the presence of ice. Since ice presence sensor probes 401 are in fixed and known positions, the ice thickness can be inferred by the presence or absence of ice at the various ice presence sensor probes 401.

The span of maximum ice thickness measurement is determined by the distance from the water surface, in this case ice-covered water surface, to the ice presence sensor probe 401 located furthest from the surface. The resolution of the ice thickness measurement is determined by the number and position of the one or more ice presence sensor probes 401. In preferred embodiment ice thickness transducer 400 illustrated in FIG. 4, the position of ice presence sensor probes 401 is linearly distributed. However, and as described already herein above, ice presence sensor probes 401 may in alternative embodiments be positioned at other locations on transducer housing 404. Further, the shape of transducer housing 404 is not critical to the present invention, and any suitable material is contemplated that provides suitable support for any ice presence sensor probes 401 and provides a liquid tight seal for ice presence sensor probes 401. The presentation of the shape of one embodiment of the transducer housing 404 is for illustrative example only and not limiting.

Preferred embodiment ice thickness transducer 400 incorporates a flotation element 432 configured to position transducer housing 404 in water 411 at or near the water surface. While the flotation element 432 may be fabricated in a vast array of suitable shapes and thicknesses, one exemplary embodiment flotation element 432 comprises a torus of closed-cell foam with brackets 430 connecting flotation element 432 to transducer housing 404. A torus provides a large open water surface, and is relatively small in cross-section comprised of only one part, so that flotation element 432 preferably does not materially alter the formation of ice in the vicinity of ice presence sensor probes 401. A solid foam sheet, such as in the form of a planar circle, would completely cover all water underneath preferred embodiment ice thickness transducer 400. This in turn would dramatically alter the freeze progress thereunder, and so will result in incorrect ice thickness reporting. Other suitable geometries will preferably provide adequate flotation while minimizing the extent of water surface coverage as much as reasonably possible. For exemplary and non-limiting purpose, such geometries in alternative embodiments will include a plurality of separate, spaced-apart flotation elements that are secured by brackets 430. The material of flotation element 432 may be any suitable material that performs the intended flotation function.

Preferred embodiment ice thickness transducer 400 incorporates a circuitry housing 450 configured to contain any required power source and circuitry to operate the one or more ice presence sensor probes 401 and provide various outputs. Circuitry housing 450 may be any shape and material suitable to perform the intended function. One exemplary and non-limiting embodiment of circuitry housing 450 is a round hollow cylinder made from Poly-Vinyl Chloride (PVC) pipe that is attached to transducer housing 404 with a watertight seal.

Preferred embodiment ice thickness transducer 400 incorporates a riser tube 452 and a display assembly 456 that provide a visual indication of the inferred thickness of the ice. Riser tube 452 raises display assembly 456 to a height sufficient to exceed any accumulation of snow on the surface of the frozen body of water 411 and thereby allow display assembly 456 to be viewed from a distance. Riser tube 452 may be any shape and the material of the riser tube 452 may be any suitable material that performs the intended function. One exemplary and non-limiting embodiment of riser tube 452 may be a round hollow cylinder made from PVC and attached to circuitry housing 450 with a watertight seal. Display assembly 456 preferably contains one or more visible indicators configured to provide a visual display of ice thickness. Many embodiments of display assembly 456 are possible. In preferred embodiment ice thickness transducer 400, four light emitting diodes (LED's) are positioned at approximately 90 degree increments that flash periodically to provide a visual indication of ice thickness. In some embodiments such as illustrated, a second digital display 454 is provided, and in other embodiments may be provided as a replacement for display assembly 456. A top cap 457 is attached to the top of display assembly 456 and provides a weather-tight seal at the top of preferred embodiment ice thickness transducer 400.

Preferred embodiment ice thickness transducer 400 incorporates a bottom cap 420 or suitable equivalent that provides a watertight seal for transducer housing 404. When preferred embodiment ice thickness transducer 400 is deployed in a body of water 411, and a person desires to keep it stationary in a particular location, a tether attachment 421, tether 422, and anchor 423 or other suitable equivalent are also provided. The representation in FIG. 4 is an approximate representation. The tether attachment 421, tether 422, and anchor 423 can be any suitable shape or material.

Figure 5:
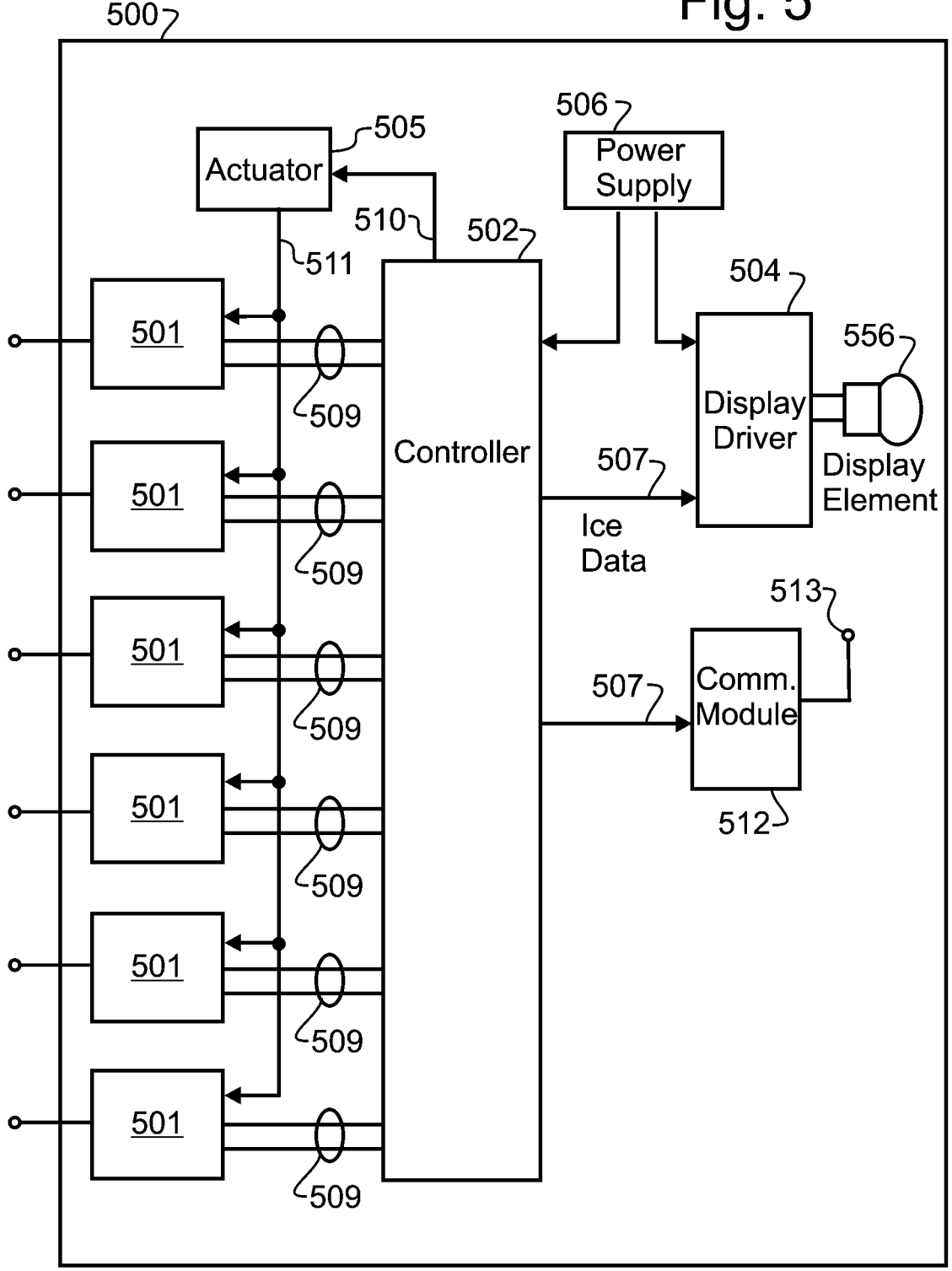
FIG. 5 shows an alternative embodiment ice thickness transducer by block diagram.

A preferred or alternative embodiment ice thickness transducer may incorporate electronic circuitry to provide determination of ice presence at one or more ice presence sensors 100, 200 such as illustrated in FIGS. 1a-1e or FIGS. 2a-2g, and provide the inferred ice thickness for display and/or subsequent processing. One exemplary embodiment of the block diagram of such electronic circuitry is presented in FIG. 5. Nevertheless, it will be understood that the system block diagram 500 in FIG. 5 is one particular embodiment and it is easily recognizable by one skilled in the art that many different embodiments are possible to perform the desired measurement, control, and display functions.

System block diagram 500 incorporates a controller 502 that periodically drives actuator 505 to provide mechanical stimulus 511 to one or more ice presence sensors 501 sensing the presence of liquid or solid in fluid media. The actuator drive signal 510 may be a DC or AC voltage of a level appropriate for use with actuator 505. One actuator 505 is illustrated, but in other embodiments multiple actuators may be employed. Controller 502 determines the state of the outputs 509 of ice presence sensors 501. The controller 502 produces ice presence data 507 responsive thereto which may be a binary representation of the presence or absence of ice at the ice presence sensors 501 when actuator 505 is energized. Display driver 504 may read the ice presence data 507 and enable one or more display elements 556 to provide a visual indication of ice thickness. The ice presence data 507 may be presented to a communication module 512 that, with an associated antenna 513, may transmit the ice presence data 507 using one of a variety of wireless communication protocols to a remote location for any of further use, analysis, or processing. Power supply 506 provides the necessary electrical energy for controller 502, display driver 504, and other associated circuitry.

Figure 6:
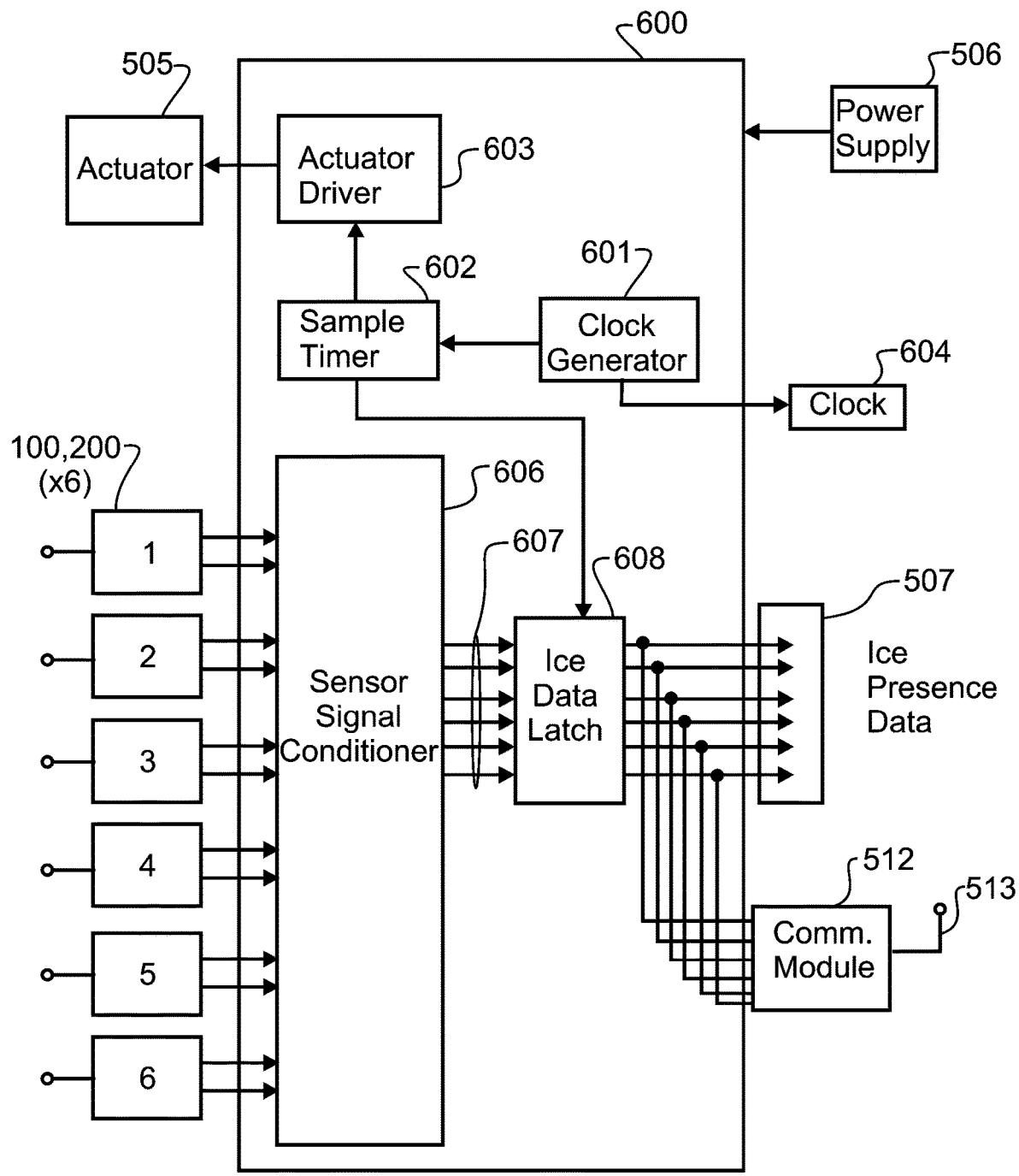
FIG. 6 shows an exemplary ice thickness transducer controller by block diagram.

FIG. 6 shows a block diagram of one exemplary six sensor controller 600. Controller 600 incorporates a clock generator 601 that generates clock pulses 604 that serves as the timing base for controller 600. Sample timer 602 may for exemplary and non-limiting purpose comprise a counter that counts the number of clock pulses received from the clock generator 601. After a preset or variable number of pulses are counted, sample timer 602 enables actuator driver 603, which momentarily energizes one or more ice presence sensor actuators 505, which might for exemplary purpose comprise actuators 105, 205 such as illustrated in FIGS.

1a-1e and 2a-2g. The actuator 505 stimulates ice presence sensors, for exemplary and non-limiting purpose such as ice presence sensors 100, 200 as previously described, and thereby causes each ice presence sensor output to assume a state corresponding to the presence or absence of ice at the sense probe such as ice presence sensor probes 101, 201. Sensor signal conditioner 606 converts the one or more ice presence sensor outputs into binary values 607 corresponding to the presence or absence of ice. FIG. 6 shows six ice presence sensors 100, 200 as an illustrative example but any number of ice presence sensors could be used as aforementioned, such as the desired resolution of the ice thickness measurement. Sample timer 602 also can enable an ice data latch 608 which stores the binary value 607 for retention until the next actuator cycle. The ice presence data 507 is one embodiment of a digital representation of the ice thickness, defined by the ice presence sensor 100, 200 output, and can be made available for display or wireless communication via communication module 512.

As may be apparent, it is easily recognizable by those skilled in the art that the block diagram of exemplary controller 600 is just one example of an implementation and a variety of implementations are possible. The block diagram 600 is shown with the use of six ice presence sensors 100, 200 as one example but it is understood that any number of ice presence sensors could be used with an implementation of the controller 600. It is also understood that controller block diagram 600 could be implemented in a variety of ways including but not limited to discrete digital logic, a programmable logic device, or a microcontroller and associated firmware.

Preferred embodiment ice thickness transducer 400 will preferably have a display assembly 456 to provide a visual indication of the measured ice thickness. FIG. 7 illustrates by block diagram one exemplary ice thickness transducer display controller 700 that controls the display assembly 456. The display controller 700 as illustrated is configured to take ice presence data 507 from FIG. 6 and actuate one or more display elements 756. FIG. 7 shows four display elements 756 for exemplary purpose, but it is understood that one display controller 700 could drive one or more display elements 756 or multiple display controllers 700 could drive multiple display elements 756. These display elements 756 may be mounted in display assembly 456 to provide an external visual indication of ice thickness. Further referring to FIG. 7, a clock 604 signal input provides the timing base for display pulse generator 702. Display pulse generator 702 converts ice presence data 507 into display element drive signals 703. The display element drive signals 703 are generated depending on the desired display of ice thickness by display element 756. Display element drive signals 703 are driven high on subsequent clock 604 pulses if the corresponding ice presence data 507 input indicates that ice is present. The logic element 704 logically combines the display element drive signals 703 in a desired manner to create a display enable 705. Display enable 705 actuates a switching element 706 which further actuates one or more display elements 756. One or more switching elements 706 and display elements 756 may be connected in parallel to provide multiple visible indicators. FIG. 7 shows four switching elements 706 and four display elements 756, but it is understood that any number of switching elements 706 can be used and one or more display elements 756 may be connected to an individual switching element. The switching element 706 is shown as a bipolar transistor for exemplary purpose only, and it is understood from the present disclosure that any of a variety of well-known switching element types may be used, such as field effect transistors, relays, or the like. Each display element 756 may comprise any device that converts electrical current to visible light, for exemplary and non-limiting purpose such as a light emitting diode or incandescent bulb. In FIG. 7 there are six inputs of ice presence data 507 as one example and it is desired that the display element illuminates sequentially once per second depending on the logical state of the ice presence data inputs 507 starting with D1 and continuing to D6.

Refer to the timing diagram 800 presented in FIG. 8 as a further illustration of one embodiment of the ice thickness transducer 400 display controller 700. A clock 604 provides the timing for the display controller 700 function. As an illustrative example assume that the clock 604 is a continuous clock pulse train with a 1 second period and a 50% duty cycle. It will be apparent to those skilled in the art that a clock 604 of any period or duty cycle may be used. The display pulse generator 702 counts clock 604 pulses and resets after a predetermined number of pulses. In the timing diagram 800 the pulse generator is reset at the end of display period 801, which in this timing diagram 800 is after 32 clock 604 pulses. The ice presence data 507 is latched in on the first clock 604 pulse. In this example there are six ice presence data 507 inputs that may be high or low depending on whether ice is present on that particular ice presence sensor 100, 200. Display element drive signals 703 are driven high on subsequent clock 604 pulses if the corresponding ice presence data 507 input indicates that ice is present. Logic element 704 logically OR's these display element drive signals 703 to create a display enable 705. In the example timing diagram 800, display elements 756 would flash once a second for four seconds and not flash for the remainder of the display period 801, since four of the ice presence data 507 inputs indicate that ice is present with a logic 1 value. After 32 clock pulses, display pulse generator 702 is reset and a new display cycle is repeated.

It will be apparent to one skilled in the art in light of the present disclosure that any number of ice presence data 507 inputs may be used in combination with alternative embodiments of display elements 756. As a non-limiting example, ice thickness transducer 400 may have twelve ice presence sensors 100, 200 contained in transducer housing 404 and these ice presence sensors 100, 200 provide twelve ice presence data 507 inputs to display pulse generator 702. Further, display enable 705 could drive two switch elements 706 to drive two display elements 756 which may be mounted in the display housing 456. In this embodiment, the display elements 756 may flash up to twelve times sequentially within the desired display period providing visual indication of ice thickness.

Referring to FIG. 9, ice thickness transducer 400 may incorporate a power supply 900 to provide the necessary electrical energy to operate internal circuitry described herein. The power source 901 may be an electrical energy storage element for the power supply and may be a primary battery, a rechargeable battery, or the like. Power source 901 may or alternatively might not be removable. The power supply may incorporate a switch 902 to turn power on and off to ice thickness transducer 400. Power source 901 may provide a positive voltage VB 905 and a common power return 903. A voltage regulator 906 may provide a regulated voltage source VCC 909 which may be used by internal circuitry described herein. If power source 901 is rechargeable, a number of known and commonly available means to recharge it may be used, for exemplary and non-limiting purpose including solar cells, USB recharging cable and the like.

It is evident from the present disclosure that an embodiment of the ice thickness transducer may be used to measure ice thickness in fluids, including but not limited to water, of varying mixtures of elements, compounds, sediments and the like. Furthermore, it is evident from the present disclosure that the ice thickness transducer may be used to measure ice thickness in water of varying configurations or depths not limited to lakes, ponds, oceans, seas, rivers, and swamps. One embodiment of the ice thickness transducer positions it at the surface of a body of water. Alternative embodiments may position the ice thickness transducer above or below the surface if desired. One embodiment of the ice thickness transducer may allow the transducer to float near or at the surface of the body of water. Alternative embodiments may rigidly fix the position of the transducer in the body of water. It is evident that there are multiple possible embodiments of the ice thickness transducer.

In accord with the teachings of the present invention, preferred embodiment sense probes such as sense probes 101, 201 have minimal movement immediately adjacent to the associated transducer housing 104, 204. Minimizing this movement requires less force generation within an actuator such as actuators 105, 205 to overcome any boundary ice formation at the boundary between transducer housing and water, while also reducing the extent of elongation or deformation of flexible membranes 103, 203. Preferred embodiment sense probes such as sense probes 101, 201 will also preferably terminate away from any boundary ice formation, allowing the end of the sense probes to accurately detect or engage with the true ice thickness formed without influence from the ice thickness transducers such as preferred embodiment ice thickness transducer 400. The mechanical probes are generally insensitive to contaminants or impurities in the water. A flotation device is also configured to also reduce influence from the ice thickness transducer to the formation of ice that will be measured.

While the foregoing details what is felt to be the preferred embodiment of the invention, no material limitations to the scope of the claimed invention are intended. Further, features and design alternatives that would be obvious to one of ordinary skill in the art are considered to be incorporated herein. The scope of the invention is set forth and particularly described in the claims herein below.

I claim:

1. An ice thickness transducer suspended adjacent a surface of a body of water, comprising:
    a transducer body having an exterior wall, an interior space, and defining a generally vertical longitudinal axis;
    an electrical power source;
    a control unit coupled with and powered by said power source;
    a buoy coupled to said transducer body and configured to locate said transducer body adjacent said surface of and within said body of water;
    at least one ice presence sensor protruding from said transducer body beyond a boundary layer between said ice thickness transducer and said water body, said at least one ice presence sensor configured to detect a presence of ice adjacent to said transducer body and beyond said boundary layer;
    said control unit coupled to said at least one ice presence sensor and configured to infer an ice thickness responsive to a detection of a presence of ice by said at least one ice presence sensor.

2. The ice thickness transducer of claim 1, further comprising a flexible waterproof membrane providing a waterproof seal between said at least one ice presence sensor and said transducer body, and to thereby isolate said transducer interior body from said body of water.

3. The ice thickness transducer of claim 2, further comprising an actuator assembly that applies a motive force to said at least one ice presence sensor tending to move said at least one ice presence sensor in said body of water beyond said boundary layer between said ice thickness transducer and said water body.

4. The ice thickness transducer of claim 3, wherein said motive force tends to rotate said at least one ice presence sensor about an ice presence sensor longitudinal axis extending in a direction radial to said transducer body longitudinal axis.

5. The ice thickness transducer of claim 3, wherein said motive force tends to rotate said at least one ice presence sensor about a pivot axis, said pivot axis extending within a plane defined by said waterproof membrane.

6. The ice thickness transducer of claim 1, further comprising a detector assembly configured to monitor a position of said at least one ice presence sensor, and responsive to said monitoring provide a liquid-indicative output when said at least one ice presence sensor is immersed in liquid and provide an ice-indicative output when said at least one ice presence sensor is immersed in ice.

7. The ice thickness transducer of claim 6, wherein said detector further comprises a switch actuated by movement of said ice presence sensor relative to said transducer body.

8. The ice thickness transducer of claim 1, wherein said at least one ice presence sensor further comprises a plurality of ice presence sensors, each one of said plurality of ice presence sensors protruding from said transducer body at a position on said transducer body vertically displaced from others of said plurality of ice presence sensors.

9. The ice thickness transducer of claim 1, further comprising a display assembly coupled to said control unit and configured to provide a quantified visual indication of said inferred ice thickness.

10. The ice thickness transducer of claim 9, wherein said display assembly further comprises at least one display element that is flashed in a coordinated manner to provide a visual indication of said inferred ice thickness.

11. The ice thickness transducer of claim 1, wherein said electrical power source and control unit are contained within said transducer body interior space.

12. An ice presence sensor monitoring a liquid-solid phase-changing fluid, comprising:
    a flexible waterproof membrane having a first face in contact with said liquid-solid phase-changing fluid and a second face isolated therefrom;
    a sense probe passing through said flexible waterproof membrane and having a first end immersed in said liquid-solid phase-changing fluid and a second end distal to said first end isolated from said liquid-solid phase-changing fluid at least by said flexible waterproof membrane, said first end protruding from said flexible waterproof membrane beyond a boundary layer between said flexible waterproof membrane and said liquid-solid phase-changing fluid;
    an actuator assembly generating a motive force urging said sense probe to rotate with respect to said flexible waterproof membrane and responsive thereto move said sense probe first end in said liquid-solid phase-changing fluid if said sense probe first end is immersed in liquid and not move said sense probe first end in said liquid-solid phase-changing fluid if said sense probe first end is immersed in solid; and a detector assembly configured to monitor movement of said sense probe responsive to said actuator assembly motive force generation and configured if said sense probe is immersed in liquid to provide a liquid-indicative output and if said sense probe is immersed in solid to provide a solid-indicative output.

13. The ice presence sensor of claim 12, wherein said motive force tends to rotate said sense probe about a sense probe longitudinal axis.

14. The ice presence sensor of claim 13, wherein said sense probe first end further comprises an arm extending transversely from said sense probe longitudinal axis.

15. The ice presence sensor of claim 12, wherein said motive force tends to rotate said sense probe about a pivot axis, said pivot axis extending within a plane defined by said flexible waterproof membrane.

16. The ice presence sensor of claim 15, wherein said sense probe first end further comprises a bulbous end.

\* \* \* \* \*